United States Patent
Clarke et al.

[11] Patent Number: 6,143,737
[45] Date of Patent: Nov. 7, 2000

[54] PROGESTERONE ANALOGS TO REVERSE MULTIDRUG RESISTANCE

[75] Inventors: Robert Clarke, Rockville, Md.; Abdel H. Talebian, Herndon, Va., Gholan Talebian, Legal Representative; Alem Ghiorghis, Silver Spring; Fabio Leonessa, Takoma Park, both of Md.; Charles Hammer, Santa Fe, N. Mex.

[73] Assignee: Georgetown University, Washington, D.C.

[21] Appl. No.: 08/667,542

[22] Filed: Jun. 21, 1996

Related U.S. Application Data
[60] Provisional application No. 60/000,440, Jun. 23, 1995.

[51] Int. Cl.$^7$ .............................. A61K 31/57; C07J 31/00
[52] U.S. Cl. ............................................ 514/177; 552/523
[58] Field of Search ............................ 552/523; 514/169, 514/177

[56] References Cited

U.S. PATENT DOCUMENTS
3,816,624  6/1974  Davis et al. ............................. 424/243
3,998,829  12/1976  Phillips et al. ......................... 260/239.5

OTHER PUBLICATIONS

Beyer et al., "Synthesis of potential antiprogestins II", Steroids, vol. 35(5), pp. 481–488, 1990.

Brueggemeier et al., "Biochemican and pharmacological development of steroidal inhibitors of aromatase", J. Steroid Biochem. Molec. Biol., vol. 37(3), pp. 379–385, 1990.

Berenbaum, M.C., "Synergy, additivism, and antagonism in immunosuppression," Clin. Exp. Immunol. 28:1–18 (1977).

Berenbaum, M.C., "The Expected Effect of a Combination of Agents: the General Solution," J. Theor. Biol. 114:413–431 (1985).

Berenbaum, M.C., "What is Synergy?" Pharmacol. Rev. 41:93–141 (1989).

Bourgain, C. et al., "Human endometrial maturation is markedly improved after luteal supplementation of gonadotropin–releasing hormone analogue/human menopausal gonadotropin stimulated cycles," Human Reproduction 9:32–40 (Jan. 1994).

Brueggemeier, R.W. & Katlic, N.E., "Effects of the Aromatase Inhibitor 7α–(4'–Amino)phenylthio–4–androstene–3,17–dione in MCF–7 Human Mammary Carcinoma Cell Culture," Cancer Research 47:4548–4551 (1987).

Brueggemeier, R.W. et al., "Biochemical and Pharmacological Development of Steroidal Inhibitors of Aromatase," J. Steroid Biochem. Molec. Biol. 37:379–385 (1990).

Clarke, R. et al., "Effect of P–glycoprotein Expression on Sensitivity to Hormones in MCF–7 Human Breast Cancer Cells," J. Natl. Cancer Inst. 84:1506–1512 (1992).

Clarke, R. & Lippman, M., "Acquisition of Antiestrogen Resistance in Breast Cancer," Drug Resistance in Oncology, Teicher, B.A., ed. Marcel Dekker, Inc., New York (1992) pp. 501–536.

Escriba, P. et al., "Role of Membrane Lipids in the Interaction of Daunomycin with Plasma Membranes from Tumor Cells: Implications in Drug–Resistance Phenomena," Biochemistry 29:7275–7282 (1990).

Fleming, G.F. et al., "Megestrol acetate reverses multidrug resistance and interacts with P–glycoprotein," Cancer Chemother. Pharmacol. 29:445–449 (1992).

Gruol, D.J. et al., "Reversal of Multidrug Resistance by RU 486," Cancer Research 54:3088–3091 (Jun. 1994).

Gulino, A. et al., "Calmodulin Antagonism and Growth–inhibiting Activity of Triphenylethylene Antiestrogens in MCF–7 Human Breast Cancer Cells," Cancer Research 46:6274–6278 (1986).

Ichikawa–Haraguchi, M. et al., "Progesterone and its metabolites: the potent inhibitors of the transporting activity of P–glycoprotein in the adrenal gland," Biochimica et Biophysica Acta 1158:201–208 (1993).

Kessel, D., "Interactions among membrane transport systems: anthracyclines, calcium antagonists and anti–estrogens," Biochem. Pharmacol. 35:2825–2826 (1986).

Lecureur, V. et al., "The antiprogestatin drug RU 486 potentiates doxorubicin cytotoxicity in multidrug resistant cells through inhibition of P–glycoprotein function," FEBS Letters 355:187–191 (Oct. 1994).

Lehnert, M. et al., "Identification of Agents for Clinical Reversal of Multidrug Resistance," Eur. J. Clin. Invest. 22:A38, No. 214 (1992).

(List continued on next page.)

Primary Examiner—Jose' G. Dees
Assistant Examiner—Barbara Badio
Attorney, Agent, or Firm—Sterne, Kessler, Goldstein & Fox P.L.L.C.

[57] ABSTRACT

The present invention is directed to compounds of formula I

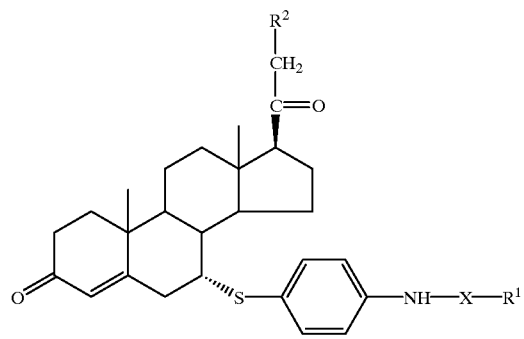

wherein the substituents are as defined in the specification. Also disclosed are compositions and method of use of the compounds.

10 Claims, 3 Drawing Sheets

OTHER PUBLICATIONS

Leonessa, F. et al., "Effect of Tamoxifen on the Multi-drug–resistant Phenotype in Human Breast Cancer Cells: Isobologram, Drug Accumulation, and $M_r$ 170,000 Glycoprotein (gp170) Binding Studies," *Cancer Research* 54:441–447 (Jan. 1994).

Loewe, S. "Antagonisms and Antagonists," *Pharmacol. Rev.* 9:237–242 (1957).

Piekarz, R.L. et al., "Progesterone Regulates the Murine Multidrug Resistance mdr1b Gene," *J. Biol. Chem.* 268:7613–7616 (1993).

Reichstein, T. & Montigel, C., "Uber Bestandteile der Nebennierenrinde und verwandte Stoffe. Einwirkung von Bleitetra–acetat auf Allopregnanolon–acetat, Pregnenolon–acetat und Progesteron," *Helv. Chim. Acta.* 22:1212–1259 (1939).

Wang, L. et al., "Reversal of the Multidrug Resistance (MDR) Phenotype with Megestrol Acetate (MA)," *Proceedings of the American Association for Cancer Research* 32:377, No. 2239 (1991).

Yang, C.–P. H., et al., "Progesterone Interacts with P–Glycoprotein in Multidrug–resistant Cells and in the Endometrium of Gravid Uterus," *J. Biol. Chem.* 264:782–788 (1989).

PROGESTERONE ANALOGS TO REVERSE MULTIDRUG RESISTANCE

This application claims the benefit of U.S. Provisional Application No. 60/000,440, filed Jun. 23, 1995.

BACKGROUND OF THE INVENTION

1. Field of the Invention

The present invention is directed to novel progesterone derivatives, as well as to pharmaceutical compositions thereof, and methods of treatment using the derivatives. More particularly, the invention relates to C7-substituted derivatives of the pregnene series.

2. Related Art

Breast cancer is the most common cancer among women living in Western societies, with almost 11% of all women living to age 80 developing the disease (Miller & Bulbrook, Int. J. Cancer 37:173–177 (1986)). Despite being an initially responsive disease (Henderson & Shapiro, "Adjuvant chemotherapy: an overview," in Medical Management of Breast Cancer, Powles & Smith, eds., Dunitz, Lindon (1991), pp. 197–215), most cytotoxic drug-responsive breast tumors, either spontaneously or following the selective pressure of systemic therapies, acquire a phenotype of multiple metastatic lesions that are resistant to all endocrine and cytotoxic therapies (Clarke, R. et al., Ann. Oncol. 1:401–407 (1990); Clarke, R. et al., Breast Cancer Res. Treat. 24:227–239 (1993); Clarke & Leonessa, "Cytotoxic drugs and hormones in breast cancer: interactions at the cellular level," in Drug and Hormonal Resistance in Breast Cancer: Cellular and Molecular Mechanisms, Dickson & Lippman, eds., Ellis Harwood, Chichester, UK (1994), pp. 407–432; Leonessa, F. et al., Acta Oncol. 31:115–123 (1991)). Since this is the major cause of death in breast cancer patients, the development of novel agents for drug-resistant breast tumors is critical.

The precise genes that confer a multidrug-resistance phenotype in breast cancer are unknown, but there are several strong single-gene candidates. These include the PGP (P-glycoprotein) product of the MDR1 gene, the multidrug-resistance-associated protein (MRP), and the altered expression of detoxification (e.g., superoxide dismutases, glutathione transferases), stress (e.g., heat-shock proteins), and other genes (e.g., topoisomerases). The precise contribution of each potential multidrug-resistance mechanism is unclear, and it is likely that more than one mechanism can operate either within the same tumor cell subpopulation and/or within different subpopulations of the same tumor.

An important resistance mechanism, and one which is the subject of the present application, is PGP-mediated resistance, a critical component of the multidrug-resistance phenotype in breast cancer when its expression is detected in tumors.

Most studies readily detect MDR1/PGP expression in breast tumors. A meta-analysis of all the published reports of MDR1/PGP expression in human breast cancers was conducted from the literature (described herein). This approach provided the ability to combine large numbers of individual patients into one study. The data from the analysis indicate that regardless of the technique applied, there is a reproducible expression of detectable levels of PGP in 25% or more of all untreated breast tumors. This value increases to an incidence of 50% of MDR1/PGP-positive tumors in treated patients ($p<0.0001$). Supporting preliminary evidence from two clinical studies that have addressed survival indicate reduced disease/progression-free survival in patients with PGP-positive breast cancers (Botti, G. et al., Tumori 79:214–218 (1993); Vernelle, P. et al., J. Natl. Cancer Inst. 83:111–116 (1991)). These data support a functional role for PGP in breast cancer. Thus, strategies to reverse PGP resistance are clearly needed.

Many of the more widely used drugs in breast cancer treatment, including the VINCA alkaloids, e.g., Vinblastine, and the anthrocycline antibiotics, e.g., Adriamycin, are substrates for PGP. The taxanes, which includes taxol, also exhibit significant activity in breast cancer and RPGP substrates (Gottesman, M. M., Cancer Res. 53:747–754 (1993)). Since PGP expression occurs in a high percentage of treated patients, there is a clear rationale for assuming that this expression can contribute to clinical resistance in these tumors.

SUMMARY OF THE INVENTION

Accordingly, the inventors have identified new, potent reversing agents using the steroid hormone progesterone, a natural PGP substrate (Yang, C. H. et al., J. Biol. Chem. 264:782–788 (1989)) as a lead compound. The inventors have conceived, designed and synthesized a novel series of C7-substituted progesterone analogs. At least one of these compounds (compound 4) is up to 35-fold more potent than progesterone, and up to 6-fold more potent (ratio of $ED_{50}$s) on an equal-molar basis than verapamil. In MCF-$7^{ADR}$ cells and in cells transfected with the MDR gene (e.g., the CL 10.3 (Clarke, R. et al., J. Natl. Cancer Inst. 84:1506–1512 (1992))) but not in sensitive control cell populations.

The present invention is directed to novel compounds having Formula I (below). Also provided is a process for preparing compounds of Formula L The novel compounds of the present invention reverse multidrug resistance, or are intermediates useful for forming compounds having this activity.

Also provided is a method of treating multidrug resistance in a mammal in need of such treatment comprising administering to said mammal an effective amount of a compound of Formula I.

Further provided is a pharmaceutical composition comprising a compound of Formula I and one or more pharmaceutically acceptable carriers or diluents.

The present invention defines a new class of multidrug-resistance reversing agents useful in chemotherapeutic protocols.

The present invention describes the structure of agents that inhibit the cellular efflux of chemotherapeutic and cytotoxic drugs.

The present invention is directed to methods for reversing the multidrug-resistance phenotype in cells, comprising administering any of the agents described herein to cells with a multidrug-resistance phenotype. The administration may be in vitro or in vivo. In highly preferred embodiments, the agents are administered to cancer patients in vivo as a means of treating tumors, and especially breast tumors, which have become multidrug-resistant. Therefore, in preferred embodiments, the complexes are coadministered with a chemotherapeutic or cytotoxic drug. In this aspect, the agents of the present invention act as a chemosensitizer or reversing agent causing the enhanced accumulation of the chemotherapeutic or cytotoxic drug as a result of the reversal of the multidrug resistance phenotype.

The complexes of the present invention may also be used in vitro to study cytotoxicity in screening protocols for new cytotoxic compounds or in tissue biopsies from cancer patients to determine effective cytotoxic agents for a particular patient.

BRIEF DESCRIPTION OF THE FIGURES

FIGS. 1A and 1B: Effect of different agents on chemosensitization to VBL (FS=old sensitization; FIG. 1A) and on VBL accumulation (FIG. 1B) in MCF-7$^{ADR}$ cells. ●=verapamil, ◆=compound 4, ◇=Compound 2, △=ZK112993, ▽=ZK98299, □=progesterone.

DETAILED DESCRIPTION OF THE PREFERRED EMBODIMENTS

The present invention is directed to compounds of Formula I:

and pharmaceutically acceptable salts and esters thereof; wherein

X is a bond, or is one of —C(O)—, —C(O)NH— or —C(O)NHSO$_2$—;

R$^1$ is one of hydrogen, alkyl, alkenyl, alkynyl, haloalkyl, dihaloalkyl, optionally substituted aralkynyl, alkoxyalkyl, aminoalkyl, cyanoalkyl, thiocyanoalkyl, azidoalkyl, optionally substituted arylalkyl, optionally substituted arylalkenyl or optionally substituted aryl; and R$^2$ is one of hydrogen, halogen, hydroxy, alkoxy, alkoxycarbonyl, alkoxymethyl, acyloxymethyl, hydroxymethyl or —OR$^3$, where R$^3$ is one of alkanoyl, a hemisuccinoyl group or benzoyl.

Preferred compounds include those wherein X is a bond, or —C(O)—, —C(O)NH— or —C(O)NHSO$_2$—; R$^1$ is hydrogen, alkyl, haloalkyl, optionally substituted aryl or optionally substituted arylalkyl; and R$^2$ is one of hydrogen, hydroxy or —OR$^3$, where R$^3$ is one of acetyl, propionyl, iso-butyryl, hemisuccinoyl or benzoyl.

Suitable values of R$^1$ include hydrogen, methyl, ethyl, propyl, butyl, chloromethyl, 2-chloroethyl, trifluoromethyl, phenyl, benzyl, phenylethyl, phenylpropyl, phenylbutyl, phenylpentyl, wherein any of said phenyl moieties are optionally substituted by one, two or three substituents independently selected from the group consisting of hydroxy, methoxy, amino, methyl and trifluoromethyl.

More preferred compounds include the compounds of Formula I wherein R$^2$ is one of hydrogen, hydroxy or acetyl, preferably hydrogen; X is —C(O)NH— or —C(O)NHSO$_2$—; and R$^1$ is phenyl or phenyl(C$_{1-8}$)alkyl, wherein the phenyl ring of either substituent may be optionally substituted with one, two or three of methyl, trifluoromethyl, methoxy, hydroxy or amino, preferably in the meta- and/or para-positions, more preferably p-methyl, p-trifluoromethyl, m,p-di(trifluoromethyl) or 3,4,5-tri(trifluoromethyl).

The present invention also includes pharmaceutically acceptable esters and salts of the compounds of Formula I, including acid addition salts.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid and the like; useful inorganic acids are hydrohalide acids such as HCl, HBr, HI, sulfuric acid, phosphoric acid and the like.

Further preferred compounds for medicinal use are compounds of Formula I that are esters of hydroxyl groups at the R$^2$ position. Preferred esters are those obtained from their corresponding acids and dioic acids: acetic, propionic, maleic, fumaric, ascorbic, pimelic, succinic, glutaric, bismethylene-salicylic, methanesulfonic, ethane-disulfonic, oxalic, tartaric, salicylic, citric, gluconic, itaconic, glycolic, p-aminobenzoic, aspartic, glutamic, gamma-amino-butyric, α-(2-hydroxyethylamino)propionic, glycine and other α-amino acids, phosphoric, sulfuric, glucuronic, and 1-methyl-1,4-dihydronicotinic.

The term "alkyl" as employed herein includes both straight and branched chain radicals of up to 12 carbons, preferably 1–8 carbons, and most preferably 1–6 carbon atoms, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the various branched chain isomers thereof.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "aralkyl" or "arylalkyl" as used herein by itself or as part of another group refers to C$_{1-6}$alkyl groups as discussed above having an aryl substituent, such as benzyl, phenethyl or 2-naphthylmethyl.

The terms "alkoxy," or "aralkoxy" includes any of the above alkyl or aralkyl groups linked to an oxygen atom.

The term "halogen" or "halo" as used herein by itself or as part of another group refers to chlorine, bromine, fluorine or iodine with chlorine being preferred.

The term "alkenyl" by itself or as part of another group as employed herein includes a carbon chain by itself or as part of another group of up to 16 carbons, preferably 2 to 10 carbons, containing one double bond such as propenyl, 2-butenyl, 3-butenyl, 2-pentenyl, 4-pentenyl and the like, and may include a halogen substituent such as I, Cl, or F.

The term "alkynyl" by itself or as part of another group as employed herein includes a carbon chain of up to 16 carbons, preferably 2 to 10 carbons, containing one triple bond such as 2-propynyl, 2-butynyl, 3-butynyl and the like.

The term "alkanoyl" as employed herein refers to straight-chained or branched alkanoyl groups having 1 to 6 carbon atoms, such as formyl, acetyl, propanoyl, n-butanoyl and pivaloyl.

The term "haloalkyl" as employed herein refers to any of the above alkyl groups substituted by one or more fluorine, chlorine, bromine or iodine atoms, e.g., fluoromethyl, difluoromethyl, trifluoromethyl and chloromethyl.

The term "aminoalkyl" as employed herein refers to any of the above alkyl groups substituted by —NH$^2$.

The term "hydroxyalkyl" as employed herein refers to any of the above alkyl groups substituted by one or more hydroxyl moieties.

The term "cyanoalkyl" as employed herein refers to any of the above alkyl groups substituted by one or more cyano moieties.

The term "thiocyanoalkyl" as employed herein refers to any of the above alkyl groups substituted by one or more thiocyano moieties.

The term "azidoalkyl" as employed herein refers to any of the above alkyl groups substituted by one or more azido moieties.

The term "optionally substituted" as employed herein refers to the presence of one or, preferably one, two or three of the following substituents: flourine, chlorine, bromine, iodine, phenyl, amino, mercapto hydroxy, methoxy, ethoxy, benzyloxy, phenoxy, benzyl, phenylethyl, alkylamino, thioalkylamino, alkylthio, alkylsulfonyl, phenylsulfonyl, alkyl or thrifluromethyl.

The steroid compounds employed as starting materials in the present invention may be prepared using conventional techniques such as are described in Djerassi, *Steroid Reactions*, Holden-Day, Inc., San Francisco (1963), or Fried and Edwards, *Organic Reactions in Steroid Chemistry*, Van Nostrand-Reinhold Co., New York (1972). Compounds that are substituted at C21 may be prepared according to the methods described in U.S. Pat. Nos. 3,998,829 and 3,816,624, and according to the methods described in Cook et al., *Human Reprod.* 9:32–39 (1994) and Reichstein et al., *Helv Chim Acta* 22:1212–1259 (1939).

The compounds of the present invention possess a C7 substitution through a thiol linkage. A novel intermediate compound, 7α-[(4'-aminophenyl)thio]-pregna4-ene-3,20-dione (1), is readily employed for the synthesis of other compounds within the scope of Formula I. This intermediate compound has a C7-thiol bridge linking primarily an aminophenyl moiety to a pregnene nucleus. Additions to the aminophenyl moiety can be readily facilitated by simple reaction with a functional group that reacts with the amino group on the aminophenyl moiety, such as an appropriate isocyanate.

Compounds where X is a bond may be formed by reacting 1 with a chloro compound, for example Cl—CH$_2$—CH$_2$—CH$_2$—CH$_2$—C$_6$H$_5$. Mono- and di-substituted compounds may be separated by reverse phase HPLC, if necessary. Compounds wherein X is —C(O)— may be formed by condensing a phenylalkyl carboxylic acid with 1, employing well-known reaction conditions for the formation of amides.

Progesterone (lead compound) was used as the starting material from which a precursor compound (6-dehydroprogesterone; pregna-4,6-diene-3,20-dione) was synthesized using Turner and Ringold's method. Compound 1 was then synthesized by direct reaction of 6-dehydroprogesterone with 4-aminothiophenol in dry dioxane.

Based on the discovery of the efficacy of C7-substituted progesterone analogs, the present invention relates to design and therapeutic uses of the analogs described herein that are transported by the multidrug resistance transport system. The invention thus provides a new class of reversing agents. The invention is therefore generally directed to a method for directly killing a cell or reversing the multidrug resistance phenotype in a multidrug resistant cell comprising administering the compounds of the present invention to the cell.

The invention is directed to a method of enhancing the intracellular accumulation of a drug in multidrug resistant cells wherein the accumulation depends upon the transport by the multidrug resistance transport system which involves P-glycoprotein. In such methods, the compounds of the present invention are coadministered with the drug.

The administration may be in vitro or in vivo. In preferred embodiments, the enhancement of accumulation of the drug in multidrug resistant cells is in vivo. In preferred embodiments of the invention, the compounds are administered to cancer patients in vivo as a means of treating tumors that have become multidrug resistant in the course of therapy.

Accordingly, chemotherapeutic agents are administered with the compounds of the present invention. The coadministration is designed to enhance accumulation of the agent following reversal of the multidrug resistant phenotype by interaction of the compounds of the present invention with the multidrug resistance transport system. Thus, the coadministration is designed to cause the chemotherapeutic agent to accumulate in amounts effective for cytotoxicity, whereas when the agent is administered alone, accummulation in effective amounts does not occur. This coadministration regimen can be applied to any cell which exhibits the multidrug resistance phenotype, for example, as a result of overexpression of the multidrug resistance protein, e.g., P-glycoprotein.

The componds of the present invention also provide methods to study cytotoxicity in vitro in a search for new cytotoxic compounds. Thus, multidrug resistant cells may be exposed in vitro to the potential cytotoxic compound in the presence of the compounds of the present invention. This regimen also allows determination of the effective combinations for chemotherapy by demonstrating which chemotherapeutic drugs can be effectively accumulated in multidrug resistant cells as a result of the addition of the compounds of the present invention. These regimens may be used in tissue biopsies to assess effective cytotoxic agents for a particular patient. Accordingly, the compounds of the present invention may be used to tailor chemotherapy to the individual patient by assessing the effect in biopsies of combinations of the compounds of the present invention and various known or potential chemotherapeutic agents.

In other embodiments of the invention, the present invention is directed to a method of enhancing the effect of a reversing agent In these embodiments, the compounds of the present invention are added to a regimen which already includes the use of a reversing agent being coadministered with a chemotherapeutic agent or other agent whose intracellular accumulation in multidrug-resistant cells is desired. Thus, the compounds of the present invention would be administered concurrently with another known reversing agent to enhance the cytotoxicity or reversing properties of the second agent Assays for the efficacy of such compounds include, but are not limited to, the ability to enhance the uptake of a chemotherapeutic agent such as daunorubicin or vincristine, the ability to block the efflux of chemotherapeutic agents from cells, the ability to interfere with photoaffinity labeling of multidrug resistant membrane vesicles, and the general ability to compete with chemosensitizing agents in any of the assays involving reversing of the multidrug resistance phenotype or binding to P-glycoprotein. Many of the methods available are in the exemplary material herein.

By the term "cell" is intended any one of the components that make up an organized tissue, consisting of a nucleus which is surrounded by cytoplasm which contains the various organelles and is enclosed in the cell or plasma membrane. For the purpose of the present invention, cells are in vivo as part of the living organism, in explanted tissue taken from a living organism, or in cell culture.

By the term "multidrug resistance" for the purpose of the present invention is intended the phenotype that occurs in a cell as the result of the overexpression of the gene product of the multidrug resistance gene or its homolog. By "multidrug resistance gene" is intended that DNA sequence which encodes P-glycoprotein and its functional equivalents and whose amplification confers upon a cell cross-resistance to toxic drugs. By "homolog" is intended the DNA sequence in another species, which sequence corresponds to the multidrug resistance gene.

By the term "administer" is intended any method for introducing the compositions of the present invention into a subject. Typical methods include, but are not limited to, oral, intranasal, parenteral (intravenous, intramuscular, or subcutaneous), or rectal. The term "administer" also relates to the application of substance ex vivo as in cell or organ culture.

When administration is for the purpose of treatment, administration may be for either prophylactic or therapeutic purposes. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

By the term "coadminister" is intended that each of at least two compounds be administered during a time frame wherein the respective periods of biological activity overlap. Thus the term includes sequential as well as coextensive administration of the compounds of the present invention.

By "compound" is intended a chemical entity, whether in the solid, liquid, or gaseous phase, which entity may be used on or administered to animals, including humans, as an aid in the diagnosis, treatment, or prevention of disease or other abnormal condition, for the relief of pain or suffering, or to control or improve any physiologic or pathologic condition. The term "compound" should be read to include synthetic compounds, natural products and macromolecular entities such as polypeptides, polynucleotides, or lipids and also small entities such as neurotransmitters, ligands, hormones or elemental compounds. The term "compound" is meant to refer to that compound whether it is in a crude mixture or purified and isolated.

By the term "transport" for the purpose of the present invention is intended the ATP-binding protein-dependent movement of a compound across the membrane of a living cell and especially where the protein is P-glycoprotein or its homologs. Transport may encompass mechanisms wherein a substrate is bound reversibly or irreversibly to the transport protein.

By the terms "chemosensitizer" or "reversing agent" are intended for the purpose of the present invention, a compound that allows the net accumulation of toxic compounds in multidrug-resistant cells equivalent to the net accumulation of said toxic compounds in non-multidrug-resistant cells. The presence of these agents may also merely increase the amount of the toxic compound able to accumulate in a multidrug resistance cell compared to the amount accumulated in the absence of the agent By the term "tumor" is intended for the purpose of the present invention, a new growth of tissue in which the multiplication of cells is uncontrolled and progressive. The tumor that is particularly relevant to the invention is the malignant tumor, one in which the primary tumor has the properties of invasion and metastasis and which shows a greater degree of anaplasia than do benign tumors. Of particular relevance to the methods and compounds described herein are malignant breast tumors.

By the term "animal" is intended any living creature that contains cells which can become multidrug resistant. Foremost among such animals are humans; however, the invention is not intended to be so-limiting, it being within the contemplation of the present invention to apply the compositions of the invention to any and all animals which may experience the benefits of the application.

By the term "over-express" is intended for the purpose of the present invention, the production of an ATP-binding cassette transport protein in a cell type in amounts exceeding that normally produced in that cell type. Although expression may vary amongst normal cell types, within each type an ATP-binding cassette transport protein is expressed within a normal physiological range. Over-expression may be due to gene amplification, an increase in RNA transcription rates, increase in RNA stability, increase in mRNA translation, or any other molecular process which results in amounts of ATP-binding cassette transport protein exceeding those amounts found in normal cells. The normal range of expression in a given cell type can be determined by routine methods as by assaying the ATP-binding cassette transport protein, its mRNA, or its gene. Assays may be those commonly used in the art such as immunoassay, PAGE, western blot, Southern and northern blots, Cot analysis, Rot analysis, and competition hybridization procedures.

By "reversing the multidrug resistance phenotype", for the purposes of the present invention, is intended causing cells, which over express the multidrug resistance gene product and therefore survive in the presence of cytotoxic agents, to become sensitive to the agents. The agents may be chemotherapeutic agents or agents which are otherwise toxic to cells. The agents are transported by the multidrug transport protein. The reversal may occur by irreversibly binding to the transport protein thereby preventing the efflux of the therapeutic compound irreversibly or by competitively inhibiting said therapeutic compound by binding the sites in the transport system ordinarily occupied by that compound. Thus the reversal may be transient or permanent.

By "efflux" is intended the transport of a chemotherapeutic compound, or other compound whose intracellular accumulation is desired, out of a cell.

The compositions according to the invention may be administered by means of the pharmaceutical or galenic formulations known and used by those skilled in the art for the particular method of administration, but preferably those used for parenteral administration, especially for intravenous, intramuscular, subcutaneous, intracutaneous, intraarticular, intrathecal, intraperitoneal infusion or injection, including continuous infusions or intermittent infusions with the pumps available to those skilled in the art, or the administration by means of micro-encapsulated preparations, e.g., based on liposomes, e.g., according to EP-A-213,523.

For preparing a ready-to-use solution for the administration of compounds according to the invention, one may use the aqueous infusible and injectable solutions known for this purpose, optionally together with the excipients, carriers and/or stabilizing substances known in the art. A ready-to-use solution for the purposes of the invention may for example be prepared by dissolving the compound in water or in phosphate-buffered physiological saline solution (pH 7 to 7.5), optionally supplemented with Tween and/or gelatine or an albumin, before administration, the solution being transferred under sterile conditions into suitable containers (e.g., syringes, ampoules, bags).

The quantity of compound to be administered for the purposes of the invention will be determined in accordance with the dosages known in the art, the severity of the disease, the response rate and the further course of the disease and side effects. Generally speaking, the dosage must be adjusted according to individual criteria.

The method of administration and dosage will depend on the therapy plans known for the above-mentioned chemotherapeutic agents, including also liposome-based microencapsulated chemotherapeutic agents.

The compounds according to the invention and conventional antimalarial substance can be administered either by simultaneous administration or by consecutive or sequential administration by suitable route, the individual active substances being provided and administered either separately, e.g., in the form of a kit or directly together. The active substance components which are present separately or either indirectly or directly together may be provided both as dry substances and as solutions, while microencapsulated forms are also possible in which the active substance components may be used directly together, indirectly as a liposome mixture or as separate systems for administration. It is advantageous for the two active substance components, the drug and compounds of the present invention to be administered simultaneously.

It is intended that any animal may be treated with the pharmaceutical compositions of the present invention. Preferably, such animal is a human, however, the invention is not intended to be so limited.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. All patents and publications cited herein are incorporated by reference herein in their entirety.

EXAMPLE 1

Preparation of 6-dehydroprogesterone(pregna-4,6-diene-3,20-dione)

A solution of gaseous HCl saturated progesterone (13.83 g, 44.1 mmol) was added to a gaseous HCl saturated solution of 2,3-dichloro-5,6-dicyano-1,4-benzoquinone (10 g, 44.1 mmol). The mixture was stirred for 30 min at room temperature and then filtered. Removal of dioxane under reduced pressure and crystallization of the resulting residue from ether gave 5.82 g of the desired compound; m.p. 127–129° C. (with decomposition).

EXAMPLE 2

Preparation of 7α-[(4'-aminophenyl)thio]-preg4-ene-3,20-dione (1)

To a mixture of 6-dehydroprogesterone (1.7 g, 5.57 mmol), 4-aminothiophenol (2.5 g, 19.65 mmol) and anhydrous dioxane (20 ml) at 60° C. was added solution metal (80 mg, 3.3. mmol). Following 5 days of siring at 60° C., the mixture was added to a stirred ice-water mix, the suspension filtered, the yellow powder taken up in boiling chloroform (150 ml), treated with activated carbon, and filtered through a bed of celite and concentrated under pressure. Crystals (1.87 g) were recovered following precipitation from a mixture of chloroform-hexane. Recrystallization from boiling dioxane yielded 1.13 g of compound 1; m.p. 183–185° C. An additional 0.195 g of compound 1 was obtained by concentrating the mother liquor to 50 ml and precipitating with ether.

EXAMPLE 3

Preparation of Various C7 Progesterone Derivatives from Compound 1

Compounds 2–5 were obtained by reacting compound 1 with the appropriate isocyanate. The reaction time for each isocyanate ranged from 2 hr to overnight, reflecting the relative reactivity of the particular isocyanate. Reaction was performed under $N_2$ purge, and the solvent removed under reduced pressure. Precipitation from ether produced the corresponding ureas. The properties of the initial series of C7 progesterone derivatives are provided in Table 1 as m.p. and methyl acetate/chloroform (1:25) TLC profiles on silica gels.

TABLE 1

Synthesis of C7-progesterone Analogues

| Compound | Isocyanate | —$R^2$ | —X— | —$R^1$ | m.p. °C. | TLC $R_f$ |
|---|---|---|---|---|---|---|
| 1 | N/A | —H | —C(O)NH— | —H | 183–185° | 0.62 |
| 2 | $CH_3CH_2NCO$ | —H | —C(O)NH— | —$CH_2CH_3$ | 225–226° | 0.41 |
| 3 | $CH_3C_6H_4SO_2NCO$ | —H | —C(O)NH— | —$SO_2C_6H_4CH_3$ | 238–240° d | — |
| 4 | $C_6H_5CH_2CH_2NCO$ | —H | —C(O)NH— | —$CH_2CH_2C_6H_5$ | 132–134° | 0.62 |
| 5 | $ClCH_2CH_2NCO$ | —H | —C(O)NH— | —$CH_2CH_2Cl$ | 177–178° | 0.52 |

TABLE 2

META-ANALYSIS OF PUBLISHED STUDIES
DESCRIBING THE EXPRESSION AND FUNCTION OF PGP/MDR1 IN HUMAN BREAST TUMORS

Effect of Treatment of PGP/MDR1 positivity in human breast tumors

| STUDY | TREATMENT | PGP/MDRI POSITIVITY | $X^2$ STATISTIC |
|---|---|---|---|
| Pooled Data-All studies | No Treatment | 25.5% positive | $\chi^2 = 31.2$ |
| (n = 17 studies) | Treatment | 49.1% positive | p < 0.0001 |
| Immunohistochemistry | No Treatment | 35.5% positive | $\chi^2 = 6.23$ |
| (n = 10 studies) | Treatment | 50.0% positive | p < 0.013 |

TABLE 2-continued

META-ANALYSIS OF PUBLISHED STUDIES
DESCRIBING THE EXPRESSION AND FUNCTION OF PGP/MDR1 IN HUMAN BREAST TUMORS

Relative Risk Assessments (risk of being PGP/MDR1 positive-treated vs. untreated) in human breast tumors
Comparison of studies that contain data on both treated and untreated tumors

| STUDY | RELATIVE RISK | 95% CL | $X^2$ TEST OF HOMOGENEITY |
|---|---|---|---|
| Pooled Data-All studies (n = 8 studies) | RR = 1.85 | CI = 1.56–2.27 | $\chi_{homog}^2$ = 5.59 (df = 6), p = 0.47 |
| Immunohistochemistry (n = 5 studies) | RR = 1.84 | CI = 1.43–2.37 | $\chi_{homog}^2$ = 2.62 (df = 4), p = 0.62 |
| Immunohistochemistry (n = 3 studies) | RR = 1.87 | CI = 1.39–2.51 | $\chi_{homog}^2$ = (insufficient data) |

Prognostic potential of PGP/MDR1 in human breast cancer (only 2 individual studies)

| STUDY | PATIENTS | MEASURE | ENDPOINT | ¶STATISTIC |
|---|---|---|---|---|
| Botti, G. et al., Tumori 79: 214–218 (1993) | n = 25 | High vs. Low | disease-free survival | p = 0.0018 (Mantel-Cox) p = 0.026 (Breslow) |
| | | | response to chemotherapy | p = 0.017 |
| Vernelle, P. et al., J Natl. Cancer Inst. 83:111–116 (1991) | n = 17 | High vs. Other | progression-free survival response to chemotherapy | p = 0.02 p = 0.02 |

*p value for test of homogeneity should be p > 0.05 for the summary relative risk estimate across the combined studies to be valid.
df = degrees of freedom; RR = relative risk; CI = confidence interval.
¶Authors' analyses/data from the references indicated.

EXAMPLE 4
Role of MDR1/PGP in Human Breast Cancer
A. Statistical Meta-analysis of Published Data on MDR1/PGP in Human Breast Tumors To directly address the potential role of MDR1/PGP and to assess previous studies, we have performed a meta-analysis of published studies obtained through extensive literature searches of several databases (e.g., Medline, Cancerlit, Current Contents, Current Advances in Cancer Research, Science Citation Index) and journals.

Pooled proportions of MDR-positive patients were derived across studies and compared between subgroups (e.g., treated vs. untreated) using methods for combining proportions from independent samples as described by Fleiss (Fleiss, J. L., *Statistical Methods for Rates and Proportions*, John Wiley & Sons, New York (1981)). There are 18 studies (Botti, G. et al., *Tumori* 79:214–218 (1993); Vernelle, P. et al., *J. Natl. Cancer Inst.* 83:111–116 (1991); Koh, E. H. et al., *Yonsei Med. J.* 33:137–142 (1992); Goldstein & Pastan, *J. Natl. Cancer Inst.* 81:116–124 (1989); Sanfilippo, O. et al., *Eur. J. Cancer* 27:155–158 (1991); Salmon, S. E. et al., *J. Natl. Cancer Inst.* 81:696–701 (1989); Merkel, D. E. et al., *J. Clin. Oncol.* 7:1129–1136 (1989); Dixon, A. R. et al., *Br. J. Cancer* 66:537–541 (1993); Hermequin, E. et al., *Breast Cancer Res. Treat.* 26:267–274 (1993); Kacinski, B. M. et al., *Cancer Communications* 1:1–6 (1989); Keith, W. N. et al., *Br. J. Cancer* 61:712–716 (1990); Moscow, J. A. et al., *Cancer Res.* 49:1422–1428 (1989); Ro, J. et al., *Hum. Pathol.* 21:787–791 (1990); Ronchi, E. et al., *Tumors* 75:542–546 (1989); Schneider, J. et al., *Br. J. Cancer* 60:815–818 (1989); Sugawara, I. et al., *Cancer Res.* 48:1926–1929 (1988); Wallner, J. et al., *Eur. J. Cancer* 27:1352–1355 (1991); Wishart, G. C. et al., *Br. J. Cancer* 62:758–761 (1990)) representing a total of 617 patients. 10 used immunohistochemistry (261 patients), and were analyzed together (Botti, G. et al., *Tumori* 79:214–218 (1993); Vernelle, P. et al., *J. Natl. Cancer Inst.* 83:111–116 (1991); Koh, E. H. et al., *Yonsei Med. J.* 33:137–142 (1992); Sanfilippo, O. et al., *Eur. J. Cancer* 27:155–158 (1991); Salmon, S. E. et al., *J. Natl. Cancer Inst.* 81:696–701 (1989); Dixon, A. R. et al., *Br. J. Cancer* 66:537–541 (1993); Ro, J. et al., *Hum. Pathol.* 21:787–791 (1990); Schneider, J. et al., *Br. J. Cancer* 60:815–818 (1989); Sugawara, I. et al., *Cancer Res.* 48:1926–1929 (1988); Wishart, G. C. et al., *Br. J. Cancer* 62:758–761 (1990)). The remaining 8 studies were considered too heterogeneous to be rationally combined for chi-squared ($\chi^2$) statistic analysis. Pooled estimates of relative risk and associated confidence intervals for MDR/PGP positivity were derived by combining study-specific logarithms of relative risks with inverse variance weights. $\chi^2$ tests of homogeneity of relative risks across studies were computed according to the Breslow-Day method. The data in Table 2 indicate a significant increase in MDR1/PGP expression in treated vs. untreated breast tumors that is independent of the detection method used or the statistical analysis applied. Over all studies, 49.1% of treated breast tumors express detectable MDR1/PGP, relative to 25.5% of untreated tumors (p<0.0001). While the number of studies assessing the effect of PGP on survival are small, these also show a significant relationship between PGP expression and poor survival (Botti, G. et al., *Tumori* 79:214–218 (1993); Vernelle, P. et al., *J. Natl. Cancer Inst.* 83:111–116 (1991)).

These meta-analyses clearly indicate that, regardless of the technique applied, there is a reproducible expression of PGP in up to 25% or more of all untreated breast tumors. This value increases to 50% positivity in treated tumors (p<0.0001: all studies), which is consistent with a significant relative risk of approximately 1.85 of a pretreated patient being PGP/MDR1 positive relative to a biopsy from an untreated patient. Both studies clearly demonstrate, with a good degree of statistical significance, the ability of PGP expression to accurately predict response/survival (Botti, G. et al., *Tumori* 79:214–218 (1993); Vernelle, P. et al., *J. Natl. Cancer Inst.* 83:111–116 (1991)). Together, these data provide compelling evidence to support the contention that MDR1/PGP plays an important role in drug resistance in human breast cancer.

EXAMPLE 5
New Models for Studying PGP-mediated Resistance

A. Cellular Models for the Study of PGP Function

Cell lines selected in vitro for resistance to ADR frequently overexpress PGP generally as a result of amplification of the MDR1 gene. Among the most widely used cell lines are the MCF-7$^{ADR}$ (Vickers, P. I. et al., *Mol. Endocrinol.* 2:886–892 (1988)) and the HeLa variant KbV series (Willingham, M. C. et al., *Cancer Res.* 46:5941–5946 (1986)). One problem with cells selected in vitro is that they frequently acquire multiple drug resistance mechanisms. For example, we have recently demonstrated that MCF-7$^{ADR}$, but not MDR1-transduced MCF-7 cells (CL 10.3), are cross-resistant to Tumor Necrosis Factor (Zyad, A. et al., *Cancer Res.* 54:825–831 (1994)). Since both ADR and Tumor Necrosis Factor can inhibit cells by the generation of free radicals (Doroshow, J. H. et al., *Free Radic. Res. Commun.* 12–13 (Pt. 2):779–781 (1991); Iwamoto & Takeda, *Hum. Cell* 3:107–112 (1990)), this cross-resistance in MCF-7$^{ADR}$ cells strongly suggests the presence of ADR resistance mechanisms in addition to PGP, including altered expression of manganous superoxide dismutase (Zyad, A. et al., *Cancer Res.* 54:825–831 (1994)). These cells also exhibit increased glutathione transferase and topoisomerase II activities (Batist, G. et al., *J. Biol. Chem.* 261:15544–15549 (1986); Sinha, B. K. et al., *Cancer Res.* 49:3844–3849 (1989)). Differences in the potency of fluphenthixol isomers identified in MCF-7$^{ADR}$ cells were not confirmed in MDR1 transfected NIH 3T3 cells (Ford, J. M. et al., *Cancer Res.* 50:1748–1756 (1990)). MCF-7$^{ADR}$ cells are of considerable utility for screening new resistance modifying agents' combinations. These cells are widely used and very well characterized, and they provide an important benchmark for comparing data among different studies. Consequently, we have incorporated the MCF-7$^{ADR}$ cells into our studies along with two cell lines transduced with a MDR1 retrieval expression vector.

It was critical to identify breast cancer cells in which we could investigate the effects of PGP reversing agents without the complicating presence of other resistance mechanisms. For example, the MCF-7$^{ADR}$ cells, which were stepwise selected for resistance to ADR, express not only increased PGP expression as a result of amplified MDR1, but elevated manganous superoxide dismutase, glutathione transferase and topoisomerase II activities (Zyad, A. et al., *Cancer Res.* 54:825–831 (1994); Batist, G. et al., *J. Biol. Chem* 261:15544–15549 (1986); Sinha, B. K. et al., *Cancer Res.* 49:3844–3849 (1989)).

B. Transduction of Hormone-Dependent MCF-7 Human Breast Cancer Cells with MDR1

Figure 1A:
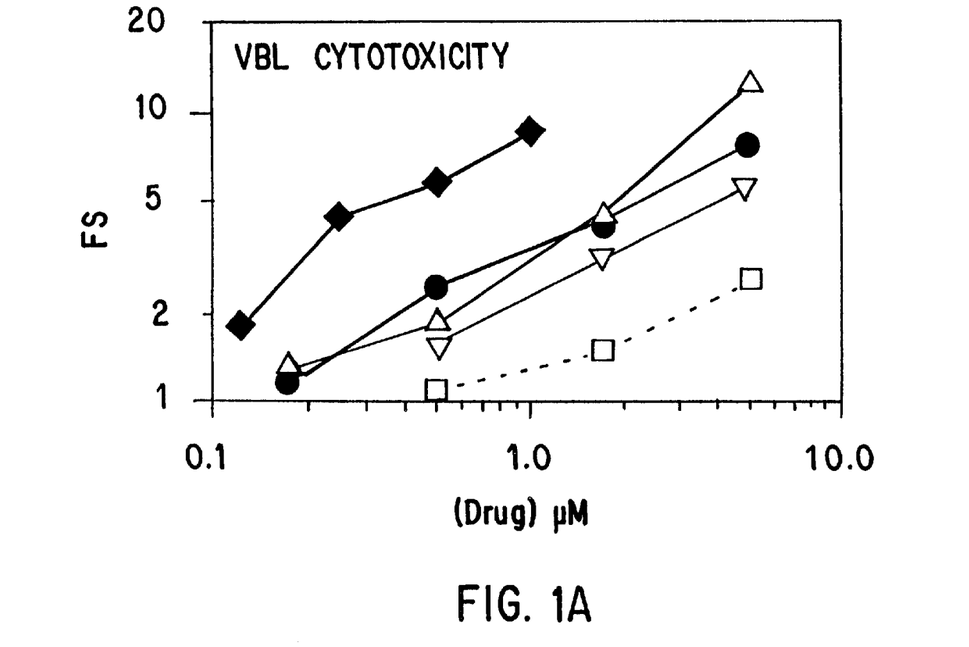
Figure 1B:
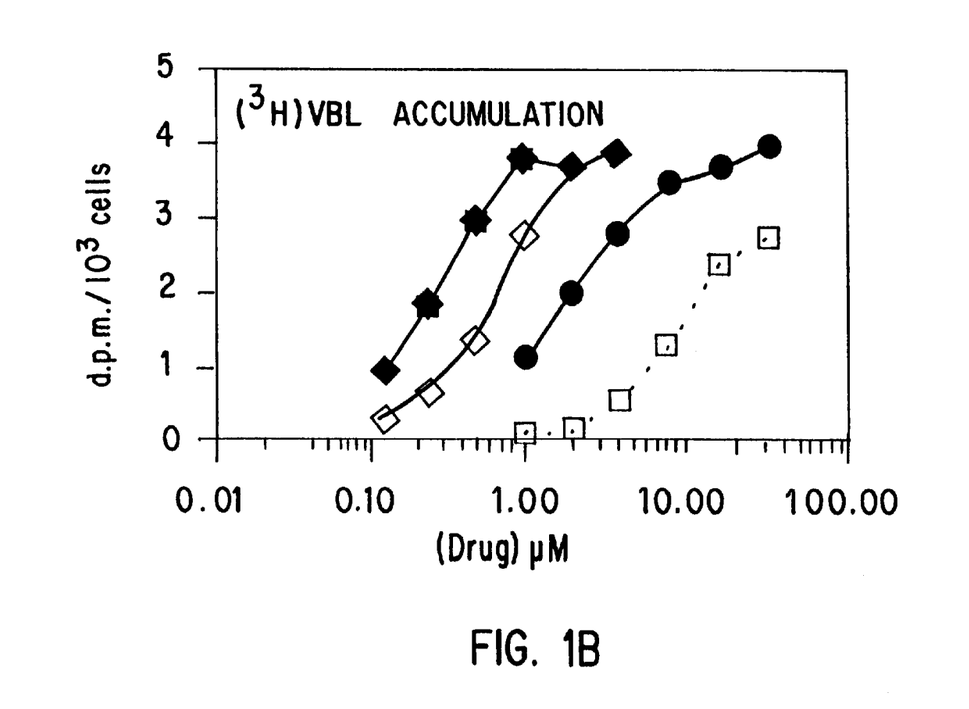
Figure 2A:
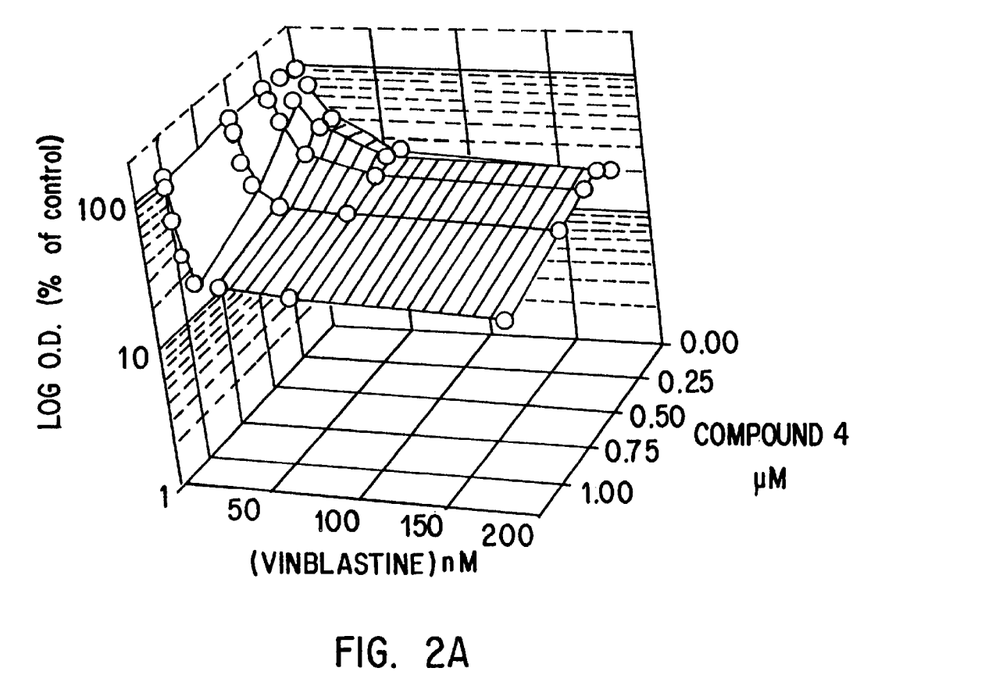
FIGS. 2A–2D: Effect of compound 4 on response (FIG. 2B) of MDA435/LCC6 (open) and MDA435/LCC$^{ADR1}$ (closed) cells to VBL, dose response surface (FIG. 2A), MDA435/LCC6MDR1 IC$_{50}$ isobol (FIG. 2D). Sensitivity Ratio=1/residual fold resistance (1.00=MDA435/LCC6) (FIG. 2C).
Figure 2B:
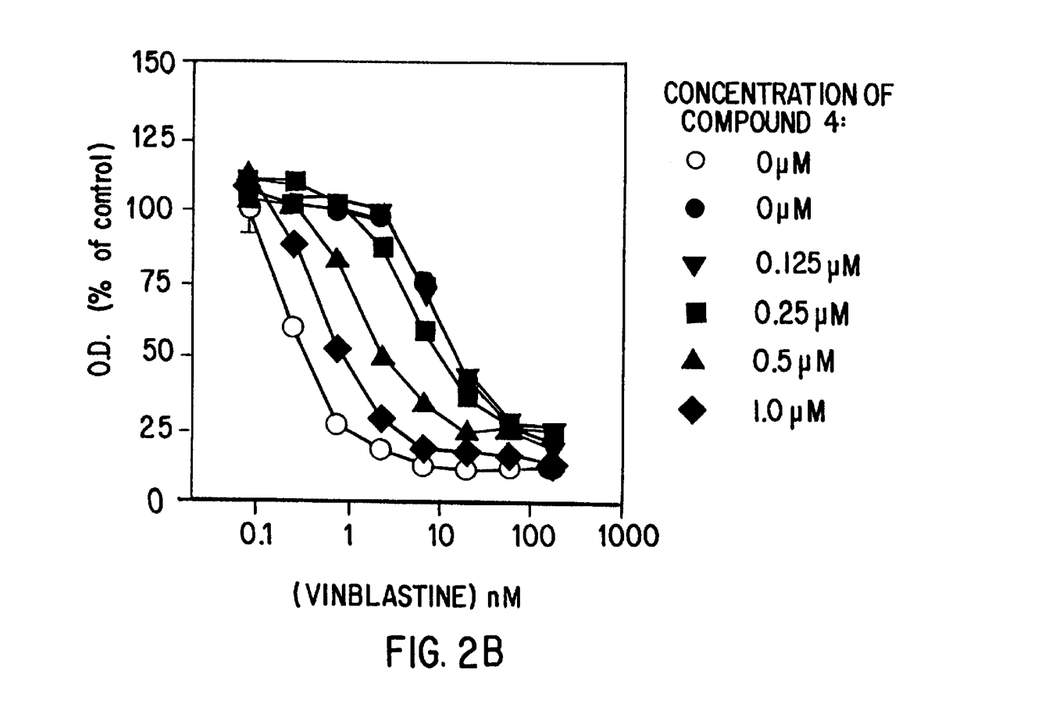
Figure 2C:
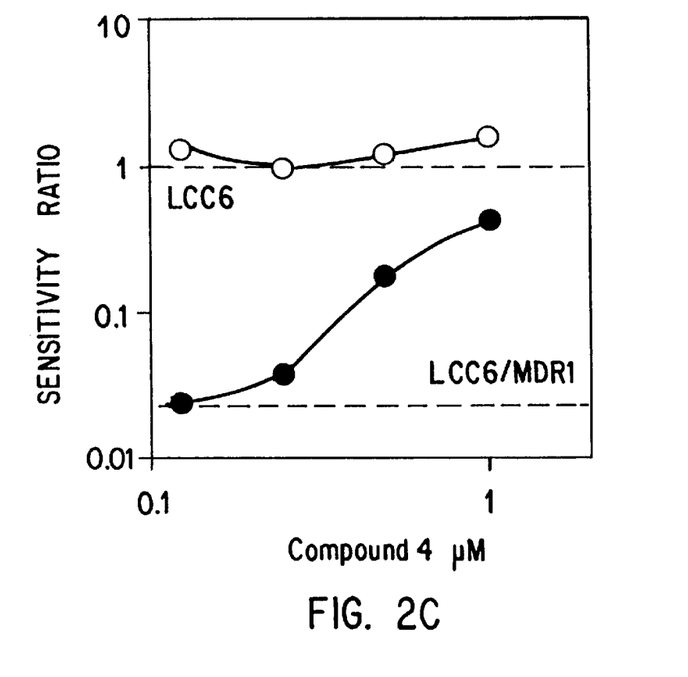
Figure 2D:
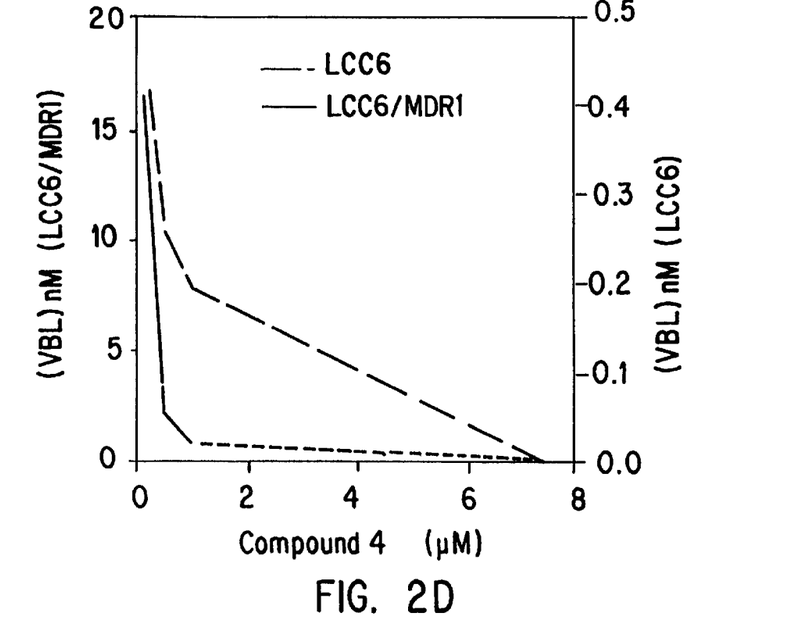

To obtain cells in which PGP is the major multidrug resistance mechanism, we transduced a cloned, E2-dependent, MCF-7 human breast cancer subline with a retroviral vector directing the constitutive expression of the MDR1 gene (Clarke, R. et al., *J. Natl. Cancer Inst.* 84:1506–1512 (1992)). Following selection in the presence of the PGP substrate colchicine, cell populations (MCF-7$^{MDR1}$) were isolated, and their ability to produce PGP determined by radioimmunoprecipitation (Clarke, R. et al., *J. Natl. Cancer Inst.* 84:1506–1512 (1992)). In this study, we have used one of the MCF-7$^{MDR1}$ clones designated CL 10.3 (FIG. 1). Transduced cells expressed high levels of a 170 kilodalton glycoprotein exhibiting immunoreactivity with specific anti-PGP antibodies. Immunoreactivity is not detected in either the parental MCF-7 cells or MCF-7 cells transduced with a control pSV2neo vector. We estimate the level of expression of MCF-7$^{MDR1}$ cells to be within 2–3 fold of that expressed by ADR-selected MCF-7$^{ADR}$ cells (Clarke, R. et al., *J. Natl. Cancer Inst.* 84:1506–1512 (1992)). The functionality of the expressed glycoprotein was confirmed by determining the sensitivity of parental and MCF-7$^{MDR1}$ cells to both a PGP substrate (ADR) and to a non-PGP substrate (gossypol). Transduced cells have a tenfold greater IC$_{50}$ for ADR, while sensitivity to gossypol is equivalent in both parental and transduced cells (Clarke, R. et al., *J. Natl. Cancer Inst.* 84:1506–1512 (1992)). We have observed a similar relationship for colchicine and the non-PGP substrate methotrexate (not shown). The increase in resistance exhibited by the transduced MCF-7$^{MDR1}$ cells would be expected to be sufficient to induce clinical resistance in tumors. We also have observed perturbations in energy metabolism in the MCF-7$^{MDR1}$ cells that are not present in the parental cells (Kaplan, O. et al., *Cancer Res.* 51:1638–1644 (1991)). MDR1-transduced cells retain ER and PGR expression, and sensitivity to the triphenylethylene antiestrogen 4-hydroxy TAM (Clarke, R. et al., *J. Natl. Cancer Inst.* 84:1506–1512 (1992)). Expression of the estrogen-inducible pS2 and EGF-receptor genes are similar in parental and MCF-7$^{MDR1}$ cells (Clarke, R. et al., *J. Natl. Cancer Inst.* 84:1506–1512 (1992)). EGF receptors in upregulated and pS2 expression is lost in MCF-7$^{ADR}$ cells (Clarke, R. et al., *J. Natl. Cancer Inst.* 84:1506–1512 (1992); Vickers, P. I. et al., *Mol. Endocrinol.* 2:886–892 (1988)). The data indicate that overexpression of the MDR1 gene alone confers a multidrug resistance phenotype, but does not result in either cross-resistance to antiestrogens or a loss of steroid hormone receptor expression (Clarke, R. et al., *J. Natl. Cancer Inst.* 84:1506–1512 (1992)).

C. An Ascites Variant (MDA435/LCC6) of the ER-negative, Invasive and Metastatic Human Breast Cancer Cell Line MDA-MB435

Approximately 26–49% of breast cancer patients develop malignant effusions (De Vita, V. T., "Principles of chemotherapy," in *Cancer: Principles and Practice of Oncology*, De Vita et al., eds., J. B. Lippincott, Philadelphia (1989), pp. 276–300). To study the properties of malignant effusions, and to develop a model for screening antineoplastic drugs, we have established a novel ascites tumor model (MDA435/LCC6) from the invasive, metastatic, and ER-negative, MDA-MB-435 human breast cancer cell line. The parental MDA-MB-435 cells were kindly provided by Dr. Janet Price (MD Anderson Cancer Center, Houston, Tex.), and were established from a pleural effusion in a 31 year old Caucasian woman with metastatic breast cancer (Caileau, R. et al., *J. Natl. Cancer Inst.* 53:661–674 (1974); Caileau, R. et al., *In Vitro* 14:911–915 (1978)). Unlike many other cell lines from breast cancer patients, this patient had received no prior systemic therapy (Dr. J. Price, personal communication) and MDA-MB-435 is one of the few human breast cancer cell lines that produce lung metastases from solid tumors (Price, J. E. et al., *Cancer Res.* 50:717–721 (1990); Meschter, C. L. et al., *Clin Exp. Metastasis* 10:167–173 (1992)).

The MDA435/LCC6 variant cells arose as a spontaneous ascites in a mouse bering a locally invasive mammary fat pad primary tumor. Polymorphic enzyme analysis of lactate dehydrogenase, glucose-6-phosphate dehydrogenase (EC 1.1.1.49), phospho-glucomutase-1 (EC 2.7.5.1), phosphoglucomutase-3 (EC 2.7.5.1), esterase D (EC 3.1.1.1), mitochondrial malic enzyme (EC 1.1.1.40), adenylate kinase (EC 2.7.4.3) and glycoxylase (EC 4.4.1.5) confirm the MDA-MB-435 origin of the MDA435/LCC6 variant. Karyotype analyses confirm the absence of mouse cells and other cell lines. MDA435/LCC6 cells grow as a monolayer culture in vitro, and as rapidly proliferating solid tumors and malignant ascites in vivo in nude mice (Wright, A. et al., *Proc. Am. Assoc. Cancer Res.* 33:490 (1992)). The ascites facilitate estimations of antitumor activity by %ILS (percent increased life span) and the solid tumors excision and growth delay analyses. MDA435/LCC6 cells can also be used in standard in vitro screening assays. The in vivo response to the PGP substrates ADR, etoposide (VP-16), mitomycin C and cisplatinum, and to the non-PGP substrate BCNU in MDA435/LCC6 ascites broadly reflects the activity of these drugs when administered as single agents in breast cancer patients (Henderson & Shapiro, "Adjuvant chemotherapy: an overview," in *Medical Management of Breast Cancer*, Powles & Smith, eds., Dunitz, Lindon (1991), pp. 197–215; Wright, A. et al., *Proc. Am. Assoc. Cancer Res.* 33:490 (1992); Millward, M. J. et al., *Br. J Cancer* 65 (suppl. XVI):42–43 (1992); Garewcal, H. S., *Semin Oncol.* 15 (suppl. 4):74–79 (1988)).

EXAMPLE 6
Previous Success in Studying Hormones/Antihromones as Reversing Agents of PGP Function A. Experimental Design and Data Analysis of in vitro Cytotoxicity assays—isobologram analysis Ford and Hait (Ford & Hait, *Biochem. Pharmacol.* 35:2825–2826 (1986)) have observed that many investigators estimate the magnitude of the effect of PGP chemosensitizing agents by directly comparing the $IC_{50}$ values for a cytotoxic drug in the presence and absence of a fixed concentration of a relatively "non-toxic" agent, by estimating the $IC_{50}$ ratios in the presence and absence of chemosensitizer alone. However, the validity of this approach decreases as the concentration of chemosensitizer approaches toxic doses, and it is inadequate in cases where the chemosensitizer exhibits inhibitory activity. The risk associated with this approach is a tendency to overestimate an interaction and assign synergy to combinations that are

TABLE 3

Derivation of the MDR1 variant cells.
Steroid hormone receptor data are presented as sites/cells and represent means of 3 or more determinations. PGR determined in the presence of E2. ND = no data (but almost certainly ER/PGR negative).

|  | ER | PGR | Reference |
|---|---|---|---|
| MCF-7 -> transduced with MDR1 expression vector -> CL 10.3 | 78,500 | 98,100 | Clarke, R. et al., J Natl. Cancer Inst. 84: 1506–1512 (1992) |
| MCF-7 -> selected in vitro against ADR -> MCF-7$^{ADR}$ | 0 | 0 | Vickers, P. I. et al., Mol. Endocrinol. 2: 886–892 (1988) |
| MDA-MB-435 (ER/PGR negative) -> nude mouse -> MDA435/LCC6 | ND | ND | Wright, A. et al., Proc. Am. Assoc. Cancer Res. 33: 490 (1992) |
| MDA435/LCC6 -> transduced with MDR1 expression vector -> MDA436/LCC6$^{MDR1}$ | ND | ND | Unpublished |

Table 3: Competitive displacement of a high affinity progestin [$^3$H] ORG2058 from PGR unlabelled ORG2058, progesterone and compound 4 from PGR in estrogen-stimulated MCF-7 human breast cancer cells. Data are expressed as % control (bound [$^3$H] ORG2058 in the absence of competitor) mean ± SD of four determinations.

Table 3: Competitive displacement of a high affinity progestin [$^3$H] ORG2058 from PGR by unlabelled ORG2058, progesterone and compound 4 from PGR in estrogen-stimulated MCF-7 human breast cancer cells. Data are expressed as % control (bound [$^3$H] ORG2058 in the absence of competitor) mean±SD of four determinations.

D. Transduction of the MDA435/LCC6 Cells with MDR1—Preliminary Characterization

MDA435/LCC6 cells were transduced with a retroviral expression vector directing the constitutive expression of the MDR1 cDNA as described previously (Clarke, R. et al., *J. Natl. Cancer Inst.* 84:1506–1512 (1992)). Expression of PgP in the transduced cells (MDA435/LCC6$^{MDR1}$) was confirmed by Western blotting (not shown), and functionally confirmed by comparing the cytotoxicity of ADR and VBL with the parental MDA435/LCC6. For VBL, the $IC_{50}$ in MDA435/LCC6$^{MDR1}$ is 23 nM, representing a 55-fold resistance relative to MDA435/LCC6. The ability to produce solid tumors in athymic nude mice also was confirmed. MDA435/LCC$^{MDR1}$ cells producing tumors with an incidence and doubling time equivalent to the parental MDA435/LCC6 cells was assessed. We are currently assessing the metastatic propoerties of these cells, since the parental cells are metastatic (Price, J. E. et al., *Cancer Res.* 50:717–721 (1990); Meschter, C. L. et al., *Clin. Exp. Metastasis* 10:167–173 (1992)).

actually additive or even subadditive/antagonistic (Berenbaum, M. C., *Pharmacol. Rev.* 41:93–141 (1989); Berenbaum, M. C., *J. Theoret. Biol.* 114:413–431 (1985)). While there are various potential methods that have been previously used to investigate drug-drug interactions (refs. 100, 102–104), Berenbaum has clearly described how the classical isobologram equation applies to drug combinations irrespective of either the shape of the constituent dose response curves (Berenbaum, M. C., *Pharmacol. Rev.* 41:93–141 (1989); Berenbaum, M. C., *J. Theoret. Biol.* 114:413–431 (1985)). In these analyses the interaction between the two drugs are represented graphically as isoeffect curves (isobolograms). A concave isobol indicates synergy, a convex isobologram reflects antagonism, and a straight line joining each axis intercept represents a zero interaction (additivity) between two drugs (Loewe, S., *Pharmacol. Rev.* 9:237–242 (1957)).

B. Reversal of PGP Resistance: Effects of TAM

TAM can inhibit all three cell lines (MCF-7, CL 10.3, MCF-7$^{ADR}$), and there are multiple potential mechanisms for TAM-induced toxicity including ER (Clarke & Lippman, "Antiestrogens resistance: mechanisms and reversal," in *Drug Resistance in Oncology*, Teicher, B. A., ed., Marcel Dekker, Inc., New York (1992), pp. 501–536), and perturbations in both membrane fluidity (Clarke, R. et al., *Biochemistry* 29:7275–7282 (1990)) and calmodulin activity (Gulino, A. et al., *Cancer Res.* 46:6274–6278 (1986)). Thus, to evaluate TAM's interactions with ADR and VBL, we performed a series of in vitro cytotoxicity assays such that the experimental data could be subjected to isobologram analyses (Berenbaum, M. C., *Pharmacol. Rev.* 41:93–141 (1989); Berenbaum, M. C., *Clin. Exp. Immunol.* 28:1–18 (1977)). These data on TAM have recently been published (Leonessa, F. et al., *Cancer Res.* 54:441–447 (1994)). The concavity of the isobols clearly indicate that TAM interacts synergistically with both ADR and VBL in the PGP-expressing MCF-7$^{ADR}$ and CL 10.3 (MCF-7$^{MDR1}$ clone). In the parental drug-sensitive MCF-7 cells, the interactions are approximately additive, although some isobols are convex indicating a slight degree of antagonism. A significant specific sensitization to VBL and ADR is observed in the CL 10.3 and MCF-7$^{ADR}$ cells, and is already detected in the presence of 1 μM TAM. Further increasing the concentration of TAM to 5 μM results in the loss of a significant synergistic interaction, and is evident for both ADR and VGL in CL 10.3 and MCF-7$^{ADR}$ cells (Leonessa, F. et al., *Cancer Res.* 54:441–447 (1994)).

C. TAM Effects on [$^3$H] VBL Accumulation and [$^3$H] Azidopine Binding to PGP

To avoid potential problems associated with additional ADR-resistance mechanisms in MCF-7$^{ADR}$ cells (e.g., manganous superoxide dismutase expression (Leonessa, F. et al., *Cancer Res.* 54:441–447 (1994)), we used VBL as the PGP substrate for the comparative binding and drug accumulation studies. We chose accumulation as our initial endpoint, since this is widely used in the literature, it reflects the combined effects of influx and efflux, and it is the final intercellular concentration of drug that determines cytotoxicity. For the drug accumulation studies we used 1 μM TAM, which will both ensure saturation of any antiestrogen binding sites (Katzenellenbogen, B. S. et al., *Breast Cancer Res. Treat.* 5:231–243 (1985)) and provide sufficient free TAM levels in the ER-positive cells. Furthermore, this concentration produces clear synergistic effects on VBL cytotoxicity in the resistant cells. TAM significantly increases [$^3$H] VBL accumulation in MCF-7$^{ADR}$ and CL 10.3 cells by approximately 3-fold, but has no effect in the parental MCF-7 cells (Leonessa, F. et al., *Cancer Res.* 54:441–447 (1994)). TAM also inhibits binding of the photoactive substrate [$^3$H] azidopine in PGP in a dose-dependent manner. The lack of a significant effect at 1 μM TAM probably reflects the relative affinities and concentrations of TAM and azidopine for PGP (Leonessa, F. et al., *Cancer Res.* 54:441–447 (1994)).

D. TAM Effects on Membrane Fluidity

Several membrane-associated functions were initially thought to confer the efflux capabilities on PGP. However, many of these including changes in membrane potential and transmembrane proton gradient, appear to have been excluded (Ruetz & Gros, *TIPS* 15:260–263 (1994)). TAM is highly lipophilic and would be expected to partition predominately into hydrophobic domains in the cell membrane, which could influence the rigidity/fluidity of the membrane and alter the function of membrane proteins. While it is possible to determine effects using artificial/synthetic membranes, the structure of cellular membranes is considerably more complex. Thus, we initially determined the ability of TAM to alter the membrane fluidity of MCF-7 (ER positive) and MDA-MB-436 (ER negative) human breast cancer cells. We used the polarization of fluorescence of the fluorophore 1,6-diphenyl-1,3,5-hexatriene to measure perturbations in global membrane fluidity (Clarke, R. et al., *Biochemistry* 29:7275–7282 (1990); Parola, A. H. et al., *Biochim. Biophys. Acta* 649:616–624 (1981)). Steady state polarization of fluorescence (P) is mainly dependent on the restriction of fluorophore rotation induced by the degree of molecular packing of the lipids (Van Blitterswijk, W. J. et al., *Biochim. Biophys. Acta* 664:323–332 (1981)), where increased packing reduces rotation and increases P.

The data (Clarke, R. et al., *Biochemistry* 29:7275–7282 (1990)) clearly indicate that TAM can significantly decrease membrane fluidity in both ER+ and ER– cells, and at concentrations where we observe significant synergy in drug resistant cells (i.e., 1 μM). These data establish the ability of TAM to significantly modify membrane function. We also have demonstrated the ability of estrogen to modify both this parameter of membrane structure, and the activity of another integral membrane protein, the folate membrane transport protein (Clarke, R. et al., *Biochemistry* 29:7275–7282 (1990); Clarke, R. et al., *Br. J Cancer* 51:365–369 (1985)).

EXAMPLE 7

Activity of the C7-Substituted Progestins

While many PGP-reversing agents have been studied, the majority are maximally active in vitro at concentrations ≥ 10 μM. It is widely acknowledged that, for many of these compounds, it is impossible to achieve this level in the sera of patients without inducing severe dose limiting toxicities (Miller, T. P. et al., *J. Clin. Oncol.* 9:17–24 (1991); Murren & Hait, *Oncology Res.* 1:1–6 (1992); Dalton, W. D. et al., *J. Clin. Oncol.* 7:415–424 (1989); Miller, R. L. et al., *J. Clin Oncol.* 6:880–888 (1988)). Our compounds were evaluated in vitro using concentrations likely to be pharmacologically relevant. 5 μM was the highest concentration, since this is the highest serum level likely to be readily achievable with a compound possessing a steroid nucleus. To determine potency relative to verapamil, we compared the equieffective concentrations. Overall, concentrations around 1 μM verapamil are probably more relevant for comparison, since this more closely reflects concentrations that can be safely achieved in the clinic (Miller, T. P. et al., *J. Clin. Oncol.* 9:17–24 (1991); Dalton, W. D. et al., *J. Clin. Oncol.* 7:415–424 (1989)). Similar serum levels of progestagens are achieved in patients receiving standard dosing, e.g. megesterol acetate (0.7 μM) (Lundgren & Lonning, *J. Steroid. Biochem.* 36:105–109 (1990)).

A. [$^3$H] VBL Accumulation of the C7-Substituted Progestins Relative to the Lead Compound (Progesterone) and Verapamil From preliminary analyses, we estimated that Compound 2 and compound 4 are the more effective of the novel C7 analogs. We then determined the relative potency for increasing [$^3$H] VBL accumulation in control (parental) and resistant cells (MCF-7$^{ADR}$) and/or MDR1 transduced in comparison with progesterone and verapamil. The concentration of compound 4 equieffective with the ED$_{50}$ of verapamil for increasing the intracellular level of VBL is 30-fold (CL 10.3) and 35-fold (MCF-7$^{ADR}$) lower than progesterone, and at concentrations 7-fold (CL 10.3) and 5-fold (MCF-7$^{ADR}$) lower than verapamil (FIG. 3: right panel). The maximal increase in intercellular VBL is equivalent to that achievable with verapamil. Compound 4 is up to 35-fold more potent than the lead compound, and up to 7-fold more potent than verapamil in increasing [$^3$H] VBL accumulation.

B. Analyses of Cytotoxicity Data of the C7-Substituted Progestins Relative to the Lead Compound (Progesterone) and Verapamil We determined the ability of compound 4 to increase the cytotoxicity of VBL. Fold sensitization by 1 μM compound 4 to VBL at VBL's IC$_{50}$ is up to 9-fold in MCF-7$^{ADR}$, and is 20-fold in the transduced MDA435/LLC6 cells (FIG. 4: upper right). The residual VBL resistance from an initial 32-fold is 3.8-fold in the MCF-7$^{ADR}$ cells in the presence of 1 µM compound 4. For MDA435/LCC6MDR1 cells, the residual VBL resistance is reduced to only 2.4-fold from an initial 49-fold resistance by 1 µM compound 4 (FIG. 4: lower right), dose response surface (FIG. 4: lower left) and isobol (FIG. 4: upper right). The comparison with other compounds is presented in the MCF-7$^{ADR}$ cells, since these cells have been widely used as a model of PGP resistance in breast cancer (FIG. 3: right panel). compound 4 is approximately 23-fold more potent than progesterone and approximately 6-fold more potent than verapamil in increasing VBL cytotoxicity.

The fold increase in both VGL accommodation and cytotoxicity induced by compound 4 are comparable, and demonstrate a consistent 6-fold or greater potency of compound 4 relative to verapamil in vitro.

C. Stability and Specificity of the C7-Substituted Progestins

Information on drug stability in serum also may be indirectly assessed by comparing effects on [$^3$H] VBL accumulation with cytotoxicity (reversing) assays using a continuous exposure. For example, Thimmaiah, K. N. et al. (*J. Med. Chem.* 35:3358–3364 (1992)) reported that some phenoxazine analogues increased [$^3$H] VBL accumulation but were ineffective at reversing VBL cytotoxicity. This proved to reflect instability of the compounds in serum-containing cell culture media (Thimmaiah, K. N. et al., *J. Med. Chem.* 35:3358–3364 (1992)). In general, steroidal structures are highly stable, and this also is true for C7-substituted androstenedione and C7-substituted 17β-estradiol. Metabolism (e.g., sulfation, hydroxylation, etc.) may occur, but would be unlikely to significantly alter the activity of the progesterone analogues. Indeed, these analogues may prove to be inhibitors of steroid metabolism, since a C7-substituted androstenedione (analogous to our compound 1) is a potent aromatase inhibitor Brueggemeier & Katlic, *Cancer Res.* 47:4548–4551 (1987); Brueggemeier, R. W. et al., *J. Steroid Biochem. Mol. Biol.* 37:379–385 (1990)). As is evident from our preliminary data, compound 4 is highly potent in both increasing [$^3$H] VBL accumulation and reversing PGP-mediated resistance.

Based on the known stability of steroids and the antiprogestins (e.g., ZK98299, ZK1 12993), compound 4 would be predicted to be a highly stable molecule. Our observations indicate that, at least by these limited criteria, compound 4 is stable in vitro. The ability of compound 4 to reverse both [$^3$H] VBL accumulation and PGP-mediated resistance in PGP-resistant, but not in the sensitive parental cells, clearly indicates that the effects of this drug are specific for PGP.

EXAMPLE 8

Methods for Testing Activity of C7-Substituted Progestins

A. Analysis of PGP Reversing Activity in vivo

The MDR1 transduced and parental cells are used, growing either as solid tumors (e.g., CL 10.3, MDA435/LCC6$^{MDR1}$) or as ascites (e.g., MDA435/LCC6$^{MDR1}$). From solid tumors, activity is assessed by perturbations in a standard tumor growth delay assay (Yamamoto, S. et al., *Cancer Lett.* 20:131–138 (1983); Corbett & Valeriote, "Rodent models in experimental chemotherapy," in *Rodent Tumor Models in Experimental Cancer Therapy*, Kallman, R. F., ed., Pergamon Press, New York (1987), pp. 233–247; Moulder & Rockwell, "Comparison of tumor assay methods," in *Rodent Tumor Models in Experimental Cancer Therapy*, Kallman, R. F., ed., Pergamon Press, New York (1987), pp. 272–278). A standard %ILS analysis is used for ascites tumors (Dhainaut, A. et al., *J. Med. Chem.* (1992); Yang, J.-M. et al., *Cancer Res.* 54:730–737 (1994)) (see below).

Animal models for breast cancer in use include human tumor and cell line xenografts, chemically induced models (e.g., DMBA), transgenic mice (e.g., c-myc, TGFα), and mammary tumor virus models (e.g., C3H mice).

B. Choice of Cytotoxic Drugs for in vivo Experiments and Their Clinical Relevance Each PGP drug used is of proven use both as a single agent and in combination chemotherapy regimens currently in use (ADR, VBL, Taxol). Non-PGP substrates are included as controls (i.e., 5-fluorouracil, methotrexate). These drugs also are used in breast cancer treatment, and can be used in human breast cancer cell lines (Clarke, R. et al., *J. Natl. Cancer Inst.* 84:1506–1512 (1992); Leonessa, F. et al., *Cancer Res.* 54:441–447 (1994); Kaplan, O. et al., *Cancer Res.* 51:1638–1644 (1991); Clarke, R. et al., *Cancer Res.* 46:6116–6119 (1986); Clarke, R. et al., *Eur. J. Cancer Clin. Oncol.* 19:19–24 (1983); van den Berg, H. W. et al, *Eur. J. Cancer Clin. Oncol.* 17:1275–1281 (1981)). For the in vivo studies, any PGP substrate (e.g., VBL, ADR, TAX) can be used, and where appropriate, a non-PGP substrate (e.g., 5-FU, with MTX as an alternate choice) can be used. Verapamil is an established PGP modulating agent.

C. Cell lines

For all MDR1/PGP studies the cell lines (selected, transduced and parental) used are shown in FIG. 1, except for experiments involving the regulation of mRNA (for which ADR-selected MCF-7 cells that do not have amplified MDR1 will be used). For PGR binding, T47D$_{co}$ cells are used. For GR binding, the CEM human lymphoblastic leukemia cells are used.

D. Drug Administration and Dosages

The reversing agent is administered before and/or concurrent with the cytotoxic drug to ensure adequate exposure during the cytotoxic agent Cytotoxic drugs are administered by tail vein injection as equitoxic doses, e.g., the approximate MTD. The objective of drug scheduling is to ensure the concurrent exposure of the tumor to maximum concentration on each drug. The drugs are administered initially as indicated below.

E. Tumor Growth Delay

Using a standard analysis (Yamamoto, S. et al., *Cancer Lett.* 20:131–138 (1983); Corbett & Valeriote, "Rodent models in experimental chemotherapy," in *Rodent Tumor Models in Experimental Cancer Therapy*, Kallman, R. F., ed., Pergamon Press, New York (1987), pp. 233–247; Moulder & Rockwell, "Comparison of tumor assay methods," in *Rodent Tumor Models in Experimental Cancer Therapy*, Kallman, R. F., ed., Pergamon Press, New York (1987), pp. 272–278), growth delay is assessed in terms of the time necessary for tumor growth in each group to increase from the initial size at the time of treatment (i.e., 0.5±2 cm$^2$), to a larger predetermined size (e.g., 1–1.5 cm$^2$). Thus, cells are inoculated into the thoracic mammary fat pads of ovariectomized nude mice, and after 2–4 weeks. When tumors have attained the appropriate mean tumor size, the animals are randomized into either the control group (vehicle only) or several treatment groups. Mice are treated, and tumor area is recorded every 2–3 days, by measuring the length of the longest axis and the width perpendicular to the longest axis, commencing on the first day of treatment. Tumor doubling times are estimated for each tumor in each group. The experiments are terminated by sacrificing the animals when the mean tumor size reaches 1–1.5 cm$^2$ in the control group and each treatment group, or after 8 weeks post treatment, as required for standard tumor growth delay assays (Yamamoto, S. et al., *Cancer Lett.* 20:131–138 (1983); Corbett & Valeriote, "Rodent models in experimental chemotherapy," in *Rodent Tumor Models in Experimental Cancer Therapy*, Kaliman, R. F., ed., Pergamon Press, New York (1987), pp. 233–247; Moulder & Rockwell, "Comparison of tumor assay methods," in *Rodent Tumor Models in Experimental Cancer Therapy*, Kallman, R. F., ed., Pergamon Press, New York (1987), pp. 272–278).

F. Excision and in vitro Colony Formation Assays

For in vivo excision analyses, tumors are established and treated as described above. Mice are sacrificed 7–10 days following treatment, to allow the cytotoxic and antihormonal drugs to have cleared from the plasma. The tumors are excised aseptically, and single-cell suspensions generated by gentle trypsinization (Hill, R. P., "Excision assays," in *Rodent Tumor Models in Experimental Cancer Therapy*, Kallman, R. F., ed., Pergamon Press, New York (1987), pp. 67–75; Namba, M. et al., *Cancer* 54:2262–2267 (1984); Mizuno & Ishida, *Biochem. Biophys. Res. Commun.* 107:1021–1027 (1982)). The in vitro colony formation assays associated with this technique is performed as described below. Statistical analyses of colony forming ability is performed using ANOVA.

G. Percent Increased Life Span (%ILS)

For the ascites model, %ILS and survival studies are performed analogous to those widely performed using the L1210 and P388 mouse leukemia models (Dhainaut, A. et al., *J. Med. Chem.* (1992); Yang, J.-M. et al., *Cancer Res.* 54:730–737 (1994)). We already have determined the %ILS of the parental MDA35/LCC6 (MDR1-negative) to most of the cytotoxic drugs to be used in this study. Briefly, $10^6$ cells are obtained from a mouse bearing an ascites of the transduced MDA35/LCC6$^{MDR1}$ cells, and inoculated into i.p. recipient mice. 24–72 hrs later the drugs are administered (depending on regimen), and the mice followed until death/morbidity.

H. Tumor Incidence (Low Tumor Burden)

For highly resistant tumors, more reliable data are obtained by determining the ability of treatments to prevent tumor formation. Cells will be inoculated on day 1, and treatment initiated 72 hrs later when the tumor burden is low. Tumor incidence and the doubling time of any arising tumors is assessed every 2–3 days. These studies are performed only if the tumor growth delay or excision assays are inconclusive/insensitive.

I. Immunohistochemistry of Tumor Tissues

The organs of all tumor bearing animals and all tumors are removed for histologic pathologic and other analyses. Tissues are removed for immunohistochemical analyses, and are fixed in 10% buffered formalin pH 7.4. Fixed tissues are mounted and stained with hematoxylin and eosin by American Histo Labs (Gaithersburg, Md.). Tissue samples for nucleic acid analyses are placed on dry ice immediately and stored at −80° C. Pathology is performed either by American Histo Labs and/or through the LCRC Tumor Bank Core Facility.

J. Receptor Binding Studies

PGR and GR binding are determined using while cell competitive binding assay described (Clarke, R. et al., *Cancer Res.* 46:6116–6119 (1986); van den Berg, H. W. et al., *Br. J. Cancer* 55:255–257 (1987); Clarke, R. et al., *Proc. Natl. Acad. Sci. USA* 86:3649–3653 (1989)). For PGR, the T47D$_{co}$ variant (ER/PGR+) is used, and for GR, a dexamethasone sensitive subclone of the CEM human acute lymphoblastic leukemia cell line is used. Briefly, cells are incubated for 60 min at 37° C. with a saturating concentration of radiolabeled steroid (e.g., 10 nM) in the absence (B$_0$) or presence of a 200-fold excess of unlabeled specific competitor (i.e., progesterone, dexamethasone (non specific biding)). For PGR, [$^3$H] ORG 2058 (specific activity 50 Ci/mmol; Amersham) is used, and for GR, [$^3$H] dexamethasone (specific activity 70 Ci/mmol; Amersham) is used. To reduce progestin binding to glucocorticoid receptors in PGR assays, cells are incubated at 37° C. with 100 nm hydrocortisone for 30 mins prior to determining PGR. Radioactivity is extracted into ethanol and measured in a liquid scintillation spectrometer. Data are analyzed using the LIGAND receptor biding software (Munson & Rodbard, *Analyt. Biochem.* 107:220–239 (1980)).

K. Statistical Analyses of in vivo Experiments

For the ascites analyses, (MDA35/LCC6; MDA435/LCC6$^{MDR1}$) percent increased life span (%ILS) is estimated. Since some animals may survive, survival curves are estimated using the Kaplan-Meie approach (Kaplan & Meier, *J. Am. Stat. Assoc.* 53:457–481 (1958)), and differences in survival between treatment groups estimated by the Log-Rank test (Mantell, N., *Cancer Chemother. Rep.* 50:163–170 (1966)). For tumor growth delay analyses (Yamamoto, S. et al., *Cancer Lett.* 20:131–138 (1983); Corbett & Valeriote, "Rodent models in experimental chemotherapy," in *Rodent Tumor Models in Experimental Cancer Therapy*, Kallman, R. F., ed., Pergamon Press, New York (1987), pp. 233–247; Moulder & Rockwell, "Comparison of tumor assay methods," in *Rodent Tumor Models in Experimental Cancer Therapy*, Kallman, R. F., ed., Pergamon Press, New York (1987), pp. 272–278), tumor growth delay is determined in terms of the time necessary for tumor growth in each group to increase from the initial size at the time of treatment (i.e., 5±2 mm), to a larger predetermined size (e.g., 10–15 mm). This approach allows evaluation of the growth inhibitory effects of the drug treatment Tumor area is recorded every 2–3 days, by measuring the length of the longest axis and the width perpendicular to the longest axis. Tumor doubling times are estimated for each individual tumor in each group, by application of Gompertzian kinetic analyses using the GROWTH software (Rygaard & Spang-Thomsen, "'GROWTH'—a computer program for determination of mean growth curves and calculation of response to therapy of solid tumor xenografts," in *Immune-Deficient Animals in Experimental Medicine*, Wu & Zhang, eds., Karger, Basel (1989), pp. 301–306). For tumor doubling time comparisons, experimental groups are compared for statistical significance by either ANOVA or multivariate ANOVA (Heitjian, D. F. et al., *Cancer Res.* 53:6042–6050 (1993)). For solid tumor (low tumor burden) studies, tumor incidence is assessed in treated and untreated (2×2 analysis using single treatment and control) by $\chi^2$. For 20 sites per group and a 50% difference in incidence, power=0.85 and α=0.05 is estimated. The tumor doubling time of tumors in treated and untreated groups (e.g., in studies of tumor incidence) is estimated. In addition to more formal $\chi^2$ studies, GEE (General Estimating Equations) methods are used to account for any lack of independence of tumors within animals. At the end of each experiment, mice are sacrificed, and the organs of all tumor bearing animals and all proliferating tumors are removed for histological examination. Tissues are fixed, mounted and stained and hematoxylin and eosin by American Histo Labs (Gaithersburg, Md.). For tumor excision assays, the colony forming ability among groups either by ANOVA or multivariate ANOVA is used.

L. In vitro Growth Assays

The growth inhibition experiments, i.e., anchorage dependent and independent assays, are designed to allow evaluation of drug interactions by isobologram analysis. Thus, they include a full definition of the dose-response curves relative to the single agents (untreated and up to 8 drug concentrations), all combinations of 5 concentrations of the modulating agent (e.g., C7 analogue) and up to 9 concentrations of the target agent. The drug concentrations necessary to achieve fixed levels of cell inhibition (from $IC_{25}$ to $IC_{80}$) in different drug combinations are estimated by interpolation within the appropriate dose-response curves as previously described (Leonessa, F. et al., *Cancer Res.* 54:441–447 (1994)). Anchorage-dependent cytotoxicity of the cytotoxic drugs, reversing agents, vehicle(s), and their appropriate chemohormonal combinations, are determined by a crystal violet assay as previously described (Leonessa, F. et al., *Cancer Res.* 54:441–447 (1994)). Dye uptake is measured by solubilization of the dye, where absorbance at 540 nm is directly related to cell number (Leonessa, F. et al., *Acta Oncol.* 31:115–123 (1991); Frandsen, T. L. et al., *Fibrinolysis* 6 (suppl. 4):71–76 (1992)). Anchorage-independent growth (colony formation in soft agar) is used as an alternative to the crystal violet assay, performed as described previously (Clarke, R. et al., *J. Endocrinol.* 122:331–340 (1989)). Briefly, cell monolayers are treated with the appropriate drugs, reversing agents and vehicle(s), the monolayers washed 3 times with growth media, gently trypsinized, and suspended in 1.5 ml growth medium containing 0.6% (w/v) agar at 41° C. The number of cells seeded varies for each cell line, reflecting the relative plating efficiency of the untreated population (MCF-7 and variants: $10^4$; MDA435/LCC6 $2\times10^3$). This agar solution is placed over a solid bottom agar layer and incubated for 10 days at 37° C. Dishes are refed with 500 $\mu$l of growth medium on days 3 and 6. Colonies of 50 cells or more (~60 $\mu$m diameter) are counted using an Omnicron electronic colony counter. Statistical analyses of colony forming ability will be performed using ANOVA.

M. Fold Sensitization and Isobologram of in vivo Growth Data

Dose-response curves of the cytotoxic drug are obtained in the absence and presence of the chemosensitizer. The curves are corrected by dividing the observed survival values by the fractional survival to the chemosensitizer alone (where present in the combination), and $IC_{50}$ values obtained by interpolation on the corrected curves. The activity of the chemosensitizer will be quantified as $FS=IC_{50}(-)/IC_{50}(+)$, where FS=Fold Sensitization, and $IC_{50}(-)$ and $IC_{50}(+)$ are the cytotoxic drug $IC_{50}$s respectively in the absence and presence of the chemosensitizer. This definition of chemosensitizing activity is adequate, assuming that the two drugs exert their cytotoxic effect as two mutually nonexclusive agents. However, this approach does not adequately handle the case of mutually exclusive agents (Rideout & Chou, "Synergism, antagonism, and potentiation in chemotherapy: an overview," in Chou & Rideout, eds., *Synergism and Antagonism in Chemotherapy*, Academic Press, San Diego (1991), pp. 3–53). Thus, a further test of the synergistic/sensitizing nature of the two drug interaction is by isobologram analysis according to the criteria defined by Berenbaum (Berenbaum, M. C., *Clin. Exp. Immunol.* 28:1–18 (1977)).

Isobologram analysis defines the nature of the interaction between two or more drugs. In a graph where the concentration of two drugs in a combination are plotted against each other, isobols are constructed uniting all isoeffective combinations of the two drugs. A concave isobol indicates synergism, a convex isobol antagonism, and a straight-line isobol zero interaction (additivity). An index of this interaction is provided by the isobologram equation (Berenbaum, M. C., *Clin. Exp. Immunol.* 28:1–18 (1977)) i.e. $I_x=d_1/D_1+d_2/D_2$ where ($D_1$) and ($D_2$) represent the respective concentrations of drug 1 and drug 2 required to produce a fixed level of inhibition ($IC_n$) when administered alone, ($d_1$) and ($d_2$) the concentrations required for the same effect when the two drugs are administered in combination, and ($I_x$) represents an index of drug interaction (Interaction Index). $I_x$ values<1 indicate synergy, 1 represents additivity, and values>1 indicate antagonism. The $I_x$ is evaluated at different levels of inhibition (i.e. $IC_{25}$–$IC_{80}$). The relative drug $IC_n$ is calculated by interpolation using the appropriate dose-response curves. We have successfully applied this approach in the analysis of the ability of TAM to modulate PGP-mediated multidrug resistance (Leonessa, F. et al., *Cancer Res.* 54:441–447 (1994)). Where an agent is non-toxic in vitro at concentrations 10-fold greater than the highest used in the combinations, there is no need to apply the isobologram analysis since any increased activity beyond that of the cytotoxic drug alone would be clearly synergistic.

EXAMPLE 9

Further Meta-Analysis of the Role of MDR1/PGP in Breast Cancer

We have continued the meta-analyses described in Example 4. We have found several additional studies, and have now identified a total of 26 studies of which we are able to use 24 in the analysis. We have also performed a more detailed statistical analysis of the published studies than previously presented. The basic principle of the meta analysis is to determine if several smaller studies can be combined into one large study, and the combined data explored to find associations and establish causes of heterogeneity among studies. The appropriateness of combining individual studies is assessed by the Breslow-Day test for homogeneity, where the p value obtained indicates the probability that the studies are too heterogeneous for combination (i.e. the p value should be greater than 0.05 indicating no significant heterogeneity). We then estimate relative risks (RR) for each association, establish a test-based confidence interval (CI), and determine the probability that this RR is significantly different from RR=1 by estimating $x^2$ by the Cochran-Mantel-Haenszel procedure and its corresponding p value.

The data for the effects of chemotherapy on MDR1/PGP expression are now too heterogeneous to enable them all to be combined for meta analysis, even if assembled as separate untreated and treated groups (e.g. Breslow-Day homogeneity $x^2=229.8$ p<0.0001 for the studies of untreated breast tumors). However, we identified a total of 7 studies that each include measurements of PGP expression in both treated and previously untreated patients (Table 4), although these are not necessarily all sequential measurements. All seven studies are sufficiently homogenous to enable them to be combined ($x^2=5.14$; p=0.40), and indicate that a breast tumor is 4 times more likely to express MDR1/PGP if it has been exposed to cytotoxic chemotherapy ($x^2=28.7$; p<0.0001 i.e. the probability that this RR is>1). Thus, there is a clear and highly significant association between MDR1/PGP expression and exposure to chemotherapy.

TABLE 4

| MDR1/PGP expression | n | Patients | $x^2$ homogeneity Breslow-Day | Relative Risk | 95% C.I. | $x^2$ Cochran-Mantel-Haenszel |
|---|---|---|---|---|---|---|
| Effect of treatment | 7* | 357 | $x^2 = 5.14$; p = 0.40 | 4.06 | 2.43–6.77 | $x^2 = 28.7$; p < 0.0001 |
| In vitro drug resistance | 3§ | 87 | $x^2 = 0.50$; p = 0.78 | 2.69 | 1.89-3.82 | $x^2 = 30.3$; p < 0.0001 |

Table 4: Pooled relative risk estimates of the risk of a tumor expressing detectable levels of MDR1/PGP (treated vs untreated), and on the RR of a tumor biopsy being resistant to ADR in vitro (MDR1/POP-positive vs (MDR1/PGP-negative). Studies combined for the effect of treatment analysis are
*= (Miller & Bulbrook, Int. J. Cancer 37: 173–177 (1986); Leonessa, F. et al., Acta Oncol. 31: 115–123 (1991)). Studies for the in vitro drug resistance analysis are
§= (Clarke, R. et al., Ann. Oncol. 1: 401–407 (1990); Botti, G. et al., Tumori 79: 214–218 (1993); Vernelle, P. et al., J. Natl. Cancer Inst. 83: 111–116 (1991));
Number in parenthesis represent appropriate literature citations.

To assess the likely functional relevance of this expression, we first combined all three published studies that assessed MDR1/PGP expression in breast cancer biopsies concurrent with the in vitro resistance of those biopsies to ADR ($x^2=0.50$; p=0.78). These analyses (Table 4) indicate that a breast tumor biopsy is 2.7-fold more likely to be resistant to ADR in vitro if it expresses detectable levels of MDR1/PGP ($x^2=30.3$; p<0.0001).

TABLE 5

| Study | n | Patients | $x^2$ homogeneity Breslow-Day | Relative Risk | 95% C.I. | $x^2$ Cochran-Mantel-Haenszel |
|---|---|---|---|---|---|---|
| All studies* | 6 | 169 | $x^2 = 7.8$; p = 0.17 | 3.35 | 2.20–5.09 | $x^2 = 32.0$; p < 0.0001 |
| PGP after Rx | 4 | 126 | $x^2 = 2.47$; p = 0.48 | 4.77 | 2.62–8.68 | $x^2 = 26.2$; p < 0.0001 |
| PGP before Rx | 2 | 59 | $x^2 = 0.44$; p = 0.51 | 2.12 | 1.15–3.91 | $x^2 = 5.72$; p < 0.017 |

Table 5: Pooled relative risk estimates of obtaining a less than partial clinical response to chemotherapy that includes a potent MDR1 drug (MDR1/PGP-positive vs MDR1/PGP-negative).
*Numbers in parentheses represent the appropriate literature citations (Clarke & Leonessa, "Cytotoxic drugs and hormones in breast cancer: interactions at the cellular level," in Drug and Hormonal Resistance in Breast Cancer: Cellular and Molecular Mechanisms, Dickson & Lippman, eds., Ellis Harwood, Chichester, UK (1994), pp. 407–432; Vernelle, P. et al., J. Natl. Cancer Inst. 83: 111–116 (1991); Gottesman, M. M., Cancer Res. 53: 747–754 (1993); Yang, C. H. et al., J. Biol. Chem. 264: 782–788 (1989); Clarke, R. et al., J. Natl. Cancer Inst. 84: 1506–1512 (1992); Clarke & Dickson, "The interactions among steroid hormone, antiestrogens, biological response modifiers and cytotoxic drugs in breast cancer," in Drug Resistance as a Biochemical Target in Cancer Chemotherapy, Tsuruo T. et al., eds., Academic Press, New York (1991), pp. 223–253.

We have also assessed the possible associations of MDR1/PGP expression in breast tumors with the RR of having a worse than partial clinical response following cytotoxic chemotherapy that contains an MDR1 drug. There are 6 clinical studies, and all can be combined for meta analysis ($x^2=7.8$; p=0.17). These produce a RR of 3.35 (Table 5), indicating that a tumor that expresses MDR1/PGP is over 30 times more likely to be found in a patient that has or will have a worse than partial clinical response to chemotherapy ($x^2=32.0$; p<0.0001). If PGP expression is measured after therapy, a PGP positive breast tumor is almost 5-times more likely to be found in a patient that exhibited a worse than partial response to a regimen that included a MDR1 drug ($x^2=26.2$; p<0.0001).

There are only two studies that measured PGP expression before treatment in untreated patients (Table 5). Nevertheless, when combined ($x^2=0.44$; p=0.51) these studies indicate that patients with PGP-positive tumors are twice as likely to subsequently exhibit a worse than partial clinical response to an MDR1 containing cytotoxic regimen ($x^2=5.72$; p=0.017).

The combined clinical studies provide compelling evidence for a likely role of PGP in the multiple drug resistance phenotype that occurs with a high frequency in patients with metastatic breast cancer. While the data remain too heterogeneous to precisely define the role of MDR1/PGP expression, they are clearly inconsistent with the concept that PGP has no role in breast cancer. There is a 5-fold increase in RR for a tumor expression PGP if that tumor was found in a patient that had obtained a worse than partial response to cytotoxic chemotherapy (6 combined studies with a total of 126 patients). Expression after chemotherapy strongly implies that there was functional PGP expression during the prior chemotherapy. Thus, these data very strongly associate PGP expression with a worse than partial clinical response (p<0.0001). This also appears consistent with the poor response rate to subsequent chemotherapy in breast cancer patients that have already relapsed following a first line cytotoxic chemotherapy. The data remain too sparse to reliably indicate the ability of PGP expression to predict subsequent response in untreated patients. While the predictive ability of PGP expression has clear implications for the clinician, this ability does not need to be established to indicate a functional role for PGP expression in breast cancer.

The results of this meta analysis provide compelling evidence for a role of MDR1/PGP in the clinical response to

What is claimed is:

1. A compound of Formula I:

or a pharmaceutically acceptable salt thereof;
wherein
X is a bond, or is one of —C(O)—, —C(O)NH— or —C(O)NHSO$_2$—;

R$^1$ is one of hydrogen, alkyl, alkenyl, alkynyl, haloalkyl, dihaloalkyl, optionally substituted aralkynyl, alkoxyalkyl, aminoalkyl, cyanoalkyl, thiocyanoalkyl, azidoalkyl, optionally substituted arylalkyl, optionally substituted arylalkenyl or optionally substituted aryl; and R$^2$ is one of hydrogen, halogen, hydroxy, alkoxy, alkoxycarbonyl, alkoxymethyl, acyloxymethyl, hydroxymethyl or —OR$^3$, where R$^3$ is one of alkanoyl, a hemisuccinoyl group or benzoyl.

2. A compound of claim 1, wherein
X is a bond, or —C(O)—, —C(O)NH— or —C(O)NHSO$_2$—;
R$^1$ is hydrogen, alkyl, haloalkyl, optionally substituted aryl or optionally substituted arylalkyl; and
R$^2$ is one of hydrogen, hydroxy or —OR$^3$, where R$^3$ is one of acetyl, propionyl, iso-butyryl, hemisuccinoyl or benzoyl.

3. A compound of claim 1, wherein
R$^1$ is hydrogen, methyl, ethyl, propyl, butyl, chloromethyl, 2-chloroethyl, trifluoromethyl, phenyl, benzyl, phenylethyl, phenylpropyl, phenylbutyl, phenylpentyl, wherein the phenyl ring of any of said phenyl ring including moieties is optionally substituted by one, two or three substituents independently selected from the group consisting of hydroxy, methoxy, amino, methyl and trifluoromethyl.

4. A compound of claim 1, wherein
X is —C(O)NH— or —C(O)NHSO$_2$—;
R$^1$ is phenyl or phenyl(C$_{1-8}$)alkyl, wherein the phenyl ring of either substituent may be optionally substituted with one, two or three of methyl, trifluoromethyl, methoxy, hydroxy or amino; and
R$^2$ is one of hydrogen, hydroxy or acetyl.

5. A compound of claim 4, wherein R$^2$ is hydrogen.

6. A compound of claim 1, wherein R$^2$ is hydrogen, X is —C(O)NH—, and R$^1$ is one of hydrogen, ethyl, p-tolylsulfonyl, phenylethyl or 2-chloroethyl.

7. A compound of claim 1, which is 7α-[(4'-aminophenyl)thio]pregna-4-ene-3,20-dione.

8. A pharmaceutically acceptable ester or acid addition salt of the compound of claim 1.

9. A pharmaceutical composition comprising the compound of claim 1 in a pharmaceutically acceptable carrier.

10. A method of reversing multidrug resistance in a multidrug resistant cell comprising administering the compound of claim 1 to said cell in an amount effective to reverse multidrug resistance in said cell.

* * * * *